US009016541B2

(12) United States Patent
Viola et al.

(10) Patent No.: US 9,016,541 B2
(45) Date of Patent: Apr. 28, 2015

(54) VARYING TISSUE COMPRESSION WITH AN ANVIL CONFIGURATION

(75) Inventors: Frank Viola, Sandy Hook, CT (US); Michael Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 1304 days.

(21) Appl. No.: 12/427,796

(22) Filed: Apr. 22, 2009

(65) Prior Publication Data

US 2009/0277949 A1    Nov. 12, 2009

Related U.S. Application Data

(60) Provisional application No. 61/051,916, filed on May 9, 2008.

(51) Int. Cl.
*A61B 17/04* (2006.01)
*A61B 17/10* (2006.01)
*A61B 17/072* (2006.01)

(52) U.S. Cl.
CPC ..... *A61B 17/072* (2013.01); *A61B 2017/07214* (2013.01); *A61B 2017/07235* (2013.01); *A61B 2017/07242* (2013.01); *A61B 2017/07264* (2013.01); *A61B 2017/07278* (2013.01)

(58) Field of Classification Search
USPC ...................... 227/175.1–182.1; 606/142, 219
See application file for complete search history.

(56) References Cited

U.S. PATENT DOCUMENTS

| 1,756,670 A | 4/1930 | Treat |
|---|---|---|
| 3,258,012 A | 6/1966 | Nakayama et al. |
| 3,744,495 A | 7/1973 | Johnson |
| 3,771,526 A | 11/1973 | Rudie |
| 3,837,555 A | 9/1974 | Green |
| 4,014,492 A | 3/1977 | Rothfuss |
| 4,278,091 A | 7/1981 | Borzone |
| 4,319,576 A | 3/1982 | Rothfuss |
| 4,475,679 A | 10/1984 | Fleury, Jr. |
| 4,527,437 A | 7/1985 | Wells |
| 4,531,522 A | 7/1985 | Bedi et al. |

(Continued)

FOREIGN PATENT DOCUMENTS

| EP | 0 129 442 | 12/1984 |
|---|---|---|
| EP | 0 169 044 | 1/1986 |

(Continued)

OTHER PUBLICATIONS

European Search Report for EP 06016963.8-2318 date of completion is Mar. 9, 2007.

(Continued)

*Primary Examiner* — Robert Long

(57) ABSTRACT

The present disclosure relates to surgical fastener applying apparatus and the application of variable compression to tissue. More specifically, the presently disclosed surgical fastener applying apparatus act to limit the flow of blood through tissue immediately adjacent a cut-line formed therein to effectuate hemostasis, while maximizing the flow of blood through tissue more removed from the cut-line to limit unnecessary necrosis. In one embodiment, a surgical fastener applying apparatus is disclosed having a tool assembly coupled to a distal end thereof with first and second jaws respectively including an anvil and a surgical fastener cartridge. The surgical fastener cartridge includes, among other things, angled pushers that engage surgical fasteners of varying lengths.

23 Claims, 17 Drawing Sheets

(56) References Cited

U.S. PATENT DOCUMENTS

| | | |
|---|---|---|
| 4,532,927 A | 8/1985 | Miksza, Jr. |
| 4,548,202 A | 10/1985 | Duncan |
| 4,573,469 A | 3/1986 | Golden et al. |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,627,437 A | 12/1986 | Bedi et al. |
| 4,741,336 A | 5/1988 | Failla et al. |
| 4,767,044 A | 8/1988 | Green |
| 4,809,695 A | 3/1989 | Gwathmey et al. |
| 4,848,637 A | 7/1989 | Pruitt |
| 4,881,545 A | 11/1989 | Isaacs et al. |
| 4,930,503 A | 6/1990 | Pruitt |
| 4,941,623 A | 7/1990 | Pruitt |
| 4,978,049 A | 12/1990 | Green |
| 5,027,834 A | 7/1991 | Pruitt |
| 5,108,422 A | 4/1992 | Green et al. |
| 5,180,092 A | 1/1993 | Crainich |
| 5,201,746 A | 4/1993 | Shichman |
| 5,209,756 A | 5/1993 | Seedhom et al. |
| 5,219,353 A | 6/1993 | Garvey, III et al. |
| 5,240,163 A | 8/1993 | Stein et al. |
| 5,282,829 A | 2/1994 | Hermes |
| 5,289,963 A * | 3/1994 | McGarry et al. ............ 227/175.1 |
| 5,342,396 A | 8/1994 | Cook |
| 5,350,400 A | 9/1994 | Esposito et al. |
| 5,352,229 A | 10/1994 | Goble et al. |
| 5,356,064 A * | 10/1994 | Green et al. ................ 227/177.1 |
| 5,364,002 A * | 11/1994 | Green et al. ................ 227/177.1 |
| 5,366,479 A * | 11/1994 | McGarry et al. .............. 606/219 |
| 5,425,489 A | 6/1995 | Shichman et al. |
| 5,439,479 A | 8/1995 | Shichman et al. |
| 5,441,193 A | 8/1995 | Smith |
| 5,452,836 A | 9/1995 | Huitema et al. |
| 5,452,837 A | 9/1995 | Williamson, IV et al. |
| 5,470,010 A | 11/1995 | Rothfuss et al. |
| 5,484,095 A | 1/1996 | Green et al. |
| 5,497,931 A | 3/1996 | Nakamura |
| 5,497,933 A * | 3/1996 | DeFonzo et al. ............ 227/175.1 |
| 5,501,693 A | 3/1996 | Gravener |
| 5,509,920 A | 4/1996 | Phillips et al. |
| 5,571,116 A | 11/1996 | Bolanos |
| 5,571,285 A | 11/1996 | Chow et al. |
| 5,584,856 A | 12/1996 | Jameel et al. |
| 5,620,452 A | 4/1997 | Yoon |
| 5,634,926 A | 6/1997 | Jobe |
| 5,667,526 A | 9/1997 | Levin |
| 5,667,527 A | 9/1997 | Cook |
| 5,676,674 A | 10/1997 | Bolanos |
| 5,697,542 A | 12/1997 | Knodel et al. |
| 5,709,680 A | 1/1998 | Yates et al. |
| 5,741,268 A | 4/1998 | Schutz |
| 5,810,822 A | 9/1998 | Mortier |
| 5,829,662 A * | 11/1998 | Allen et al. ................ 227/177.1 |
| 5,865,361 A | 2/1999 | Milliman |
| 5,871,135 A | 2/1999 | Williamson, IV et al. |
| 5,879,371 A | 3/1999 | Gardiner et al. |
| 5,915,616 A | 6/1999 | Viola et al. |
| 5,961,521 A | 10/1999 | Roger |
| 5,964,394 A | 10/1999 | Robertson |
| 6,083,242 A | 7/2000 | Cook |
| 6,202,914 B1 | 3/2001 | Geiste et al. |
| 6,273,897 B1 | 8/2001 | Dalessandro et al. |
| 6,325,810 B1 | 12/2001 | Hamilton et al. |
| 6,348,054 B1 | 2/2002 | Allen |
| 6,450,391 B1 * | 9/2002 | Kayan et al. ................ 227/176.1 |
| 6,706,057 B1 | 3/2004 | Bidoia et al. |
| 6,786,382 B1 | 9/2004 | Hoffman |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,001,411 B1 | 2/2006 | Dean |
| 7,044,352 B2 | 5/2006 | Shelton, IV et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,377,928 B2 | 5/2008 | Nguyen |
| 7,398,908 B2 | 7/2008 | Holsten et al. |
| 7,407,076 B2 | 8/2008 | Racenet |
| 7,455,676 B2 | 11/2008 | Holsten et al. |
| 7,500,979 B2 | 3/2009 | Hueil et al. |
| 7,547,312 B2 | 6/2009 | Woo |
| 7,604,151 B2 * | 10/2009 | Hess et al. ................. 227/181.1 |
| 7,624,903 B2 * | 12/2009 | Green et al. ................ 227/179.1 |
| 7,641,091 B2 | 1/2010 | Olson |
| 7,794,475 B2 | 9/2010 | Hess |
| 7,819,896 B2 * | 10/2010 | Racenet ....................... 606/219 |
| 7,866,526 B2 * | 1/2011 | Green et al. ................ 227/175.1 |
| 8,372,094 B2 | 2/2013 | Severson |
| 8,720,766 B2 | 5/2014 | Hess |
| 2002/0117534 A1 * | 8/2002 | Green et al. ................ 227/176.1 |
| 2004/0004105 A1 | 1/2004 | Jankowski |
| 2004/0073222 A1 | 4/2004 | Koseki |
| 2004/0173659 A1 * | 9/2004 | Green et al. ................ 227/176.1 |
| 2004/0232195 A1 | 11/2004 | Shelton et al. |
| 2004/0232199 A1 | 11/2004 | Shelton et al. |
| 2004/0247415 A1 | 12/2004 | Mangone, Jr. |
| 2005/0006430 A1 | 1/2005 | Wales |
| 2005/0006431 A1 | 1/2005 | Shelton et al. |
| 2005/0006434 A1 | 1/2005 | Wales |
| 2005/0023324 A1 | 2/2005 | Doll et al. |
| 2005/0023325 A1 | 2/2005 | Gresham et al. |
| 2005/0070925 A1 | 3/2005 | Shelton, IV et al. |
| 2005/0070958 A1 | 3/2005 | Swayze et al. |
| 2005/0173490 A1 | 8/2005 | Shelton, IV |
| 2005/0178813 A1 | 8/2005 | Swayze et al. |
| 2005/0187576 A1 | 8/2005 | Whitman et al. |
| 2005/0263562 A1 | 12/2005 | Shelton, IV et al. |
| 2005/0267530 A1 | 12/2005 | Cummins |
| 2006/0000868 A1 | 1/2006 | Shelton, IV et al. |
| 2006/0015144 A1 | 1/2006 | Burbank et al. |
| 2006/0022014 A1 | 2/2006 | Shelton, IV et al. |
| 2006/0022015 A1 | 2/2006 | Shelton, IV et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton, IV et al. |
| 2006/0025816 A1 | 2/2006 | Shelton, IV |
| 2006/0025817 A1 | 2/2006 | Ortiz et al. |
| 2006/0039779 A1 | 2/2006 | Ring |
| 2006/0049230 A1 | 3/2006 | Shelton, IV et al. |
| 2006/0097026 A1 | 5/2006 | Shelton, IV |
| 2006/0124688 A1 | 6/2006 | Racenet et al. |
| 2006/0163312 A1 | 7/2006 | Viola et al. |
| 2006/0226196 A1 | 10/2006 | Hueil et al. |
| 2006/0291981 A1 | 12/2006 | Viola |
| 2007/0010838 A1 | 1/2007 | Shelton, IV et al. |
| 2007/0075115 A1 * | 4/2007 | Olson et al. ................ 227/175.1 |
| 2007/0084899 A1 * | 4/2007 | Taylor ....................... 227/176.1 |
| 2007/0131732 A1 | 6/2007 | Holsten et al. |
| 2007/0262116 A1 | 11/2007 | Hueil et al. |
| 2008/0041918 A1 | 2/2008 | Holsten et al. |
| 2008/0078804 A1 | 4/2008 | Shelton et al. |
| 2009/0105535 A1 * | 4/2009 | Green et al. ................... 600/106 |
| 2009/0308908 A1 * | 12/2009 | Green et al. ................ 227/176.1 |
| 2009/0314820 A1 * | 12/2009 | Green et al. ................ 227/176.1 |
| 2010/0327042 A1 * | 12/2010 | Amid et al. ................ 227/176.1 |

FOREIGN PATENT DOCUMENTS

| | | |
|---|---|---|
| EP | 0588081 | 3/1994 |
| EP | 0878169 | 11/1998 |
| EP | 0640315 | 12/1998 |
| EP | 1090592 | 4/2001 |
| EP | 1316290 | 6/2003 |
| EP | 1479346 | 11/2004 |
| EP | 1728473 | 12/2006 |
| EP | 1 754 445 A2 | 2/2007 |

(56) References Cited

FOREIGN PATENT DOCUMENTS

| | | |
|---|---|---|
| EP | 1 785 098 A2 | 5/2007 |
| EP | 1 875 868 | 1/2008 |
| EP | 1875868 A | 1/2008 |
| EP | 1 917 918 A2 | 5/2008 |
| EP | 1 971 918 | 5/2008 |
| EP | 2 095 777 | 9/2009 |
| FR | 2838952 | 10/2003 |
| GB | 2 019 296 | 10/1979 |
| GB | 2 029 754 | 3/1980 |
| GB | 2 051 287 | 1/1981 |
| SU | 405234 | 9/1975 |
| SU | 1333319 | 8/1987 |
| SU | 1442191 | 12/1988 |
| SU | 1459659 | 2/1989 |
| WO | WO 86/02254 A1 | 4/1986 |
| WO | WO 90/05489 | 5/1990 |
| WO | WO 96/19146 | 6/1996 |
| WO | WO 97/34533 | 9/1997 |
| WO | WO02/30296 | 4/2002 |
| WO | WO 03/094743 | 11/2003 |
| WO | WO 03/094747 | 11/2003 |
| WO | WO2006/055385 | 5/2006 |
| WO | WO 2008/007377 | 1/2008 |
| WO | WO 2008/039250 | 4/2008 |
| WO | WO2008/089050 | 7/2008 |

OTHER PUBLICATIONS

European Search Report for EP 06016963.8-2318 date of completion is Mar. 9, 2007 (9 pages).
European Search Report dated Jan. 31, 2011 for European Patent Appln. No. EP 10 25 1797.
International Search Report from EP Application No. 07 25 4366 dated Nov. 11, 2010.
International Search Report from EP Application No. 09 25 1067 mailed Mar. 17, 2011.
European Search Report for EP 11004299.1269 date of completion is Aug. 2, 2011 (3 pages).
European Search Report EP08 25 2283 dated Jan. 15, 2009.
European Search Report EP09 25 1224.3-2310 dated Oct. 8, 2009.
European Search Report EP09 251268.0-2310 dated Nov. 16, 2009.
European Search Report EP11004299.1269 dated Aug. 12, 2011.
European Search Report EP9251240.9 dated Oct. 19, 2009.

* cited by examiner

VARYING TISSUE COMPRESSION WITH AN ANVIL CONFIGURATION

CROSS-REFERENCE TO RELATED APPLICATIONS

This application claims the benefit of, and priority to, U.S. Provisional Pat. Application Ser. No. 61/051,916, filed May 9, 2008, the entire contents of which are incorporated by reference herein.

BACKGROUND

1. Technical Field

The present disclosure relates to surgical fastener applying apparatus. More particularly, the present disclosure relates to a tool assembly for use with a surgical fastener applying apparatus, and methods of manufacturing the same, to apply a plurality of surgical fasteners to tissue with varying compressive forces.

2. Background of the Related Art

Many varieties of surgical fastener applying apparatus are known in the art, some of which are specifically adapted for use in various surgical procedures including, but not limited to, end-to-end anastomosis, circular end-to-end anastomosis, open gastrointestinal anastomosis, endoscopic gastrointestinal anastomosis, and transverse anastomosis. Suitable examples of apparatus which may be used during the course of these procedures can be seen in U.S. Pat. Nos. 5,915,616; 6,202,914; 5,865,361; and 5,964,394.

In general, a surgical fastener applying apparatus will include an anvil that is approximated relative to a surgical fastener cartridge during use. The anvil includes depressions that are aligned with, and/or are in registration with, slots defined in the surgical fastener cartridge, through which the surgical fasteners will emerge. To effectuate formation, the surgical fasteners emerge from the surgical fastener cartridge and are driven against the anvil. The surgical fastener cartridge typically has one or more rows of surgical fasteners that are disposed laterally outward of a slot that is configured to accommodate a knife, or other such cutting element, such that tissue can be simultaneously severed and joined together at a cut-line. Depending upon the particular surgical fastener applying apparatus, the rows of fasteners may be arranged in a linear, non-linear, e.g. circular, semi-circular, or other configuration.

Various types of surgical fasteners are well known in the art including, but not limited to, unitary fasteners and two-part fasteners. Unitary fasteners generally include a pair of legs that are adapted to penetrate tissue and connected by a backspan from which they extend. In use, subsequent to formation, certain types of unitary fasteners have a "B" shaped configuration. Typically, the two-part fastener includes legs that are barbed and connected by a backspan. The legs are engaged and locked into a separate retainer piece that is usually located in the anvil. In use, the two-part fastener is pressed into the tissue so that the barbs penetrate the tissue and emerge from the other side where they are then locked into the retainer piece. The retainers prevent the two-part fastener from dislodging from the tissue. The two-part fasteners are not intended to be unlocked or removable. For this reason, they are generally made of a bioabsorbable material.

A common concern in each of the procedures mentioned above is hemostasis, or the rate at which bleeding of the target tissue is stopped. It is commonly known that by increasing the amount of pressure applied to a wound, the flow of blood can be limited, thereby decreasing the time necessary to achieve hemostasis. To this end, conventional surgical fastener applying apparatus generally apply two or more rows of fasteners about the cut-line to compress the surrounding tissue in an effort to stop any bleeding and to join the cut tissue together. Each of the surgical fasteners will generally apply a compressive force to the tissue that is sufficient to effectuate hemostasis. However, applying too much pressure can result in a needless reduction in blood flow to the tissue surrounding the cut-line, resulting in an elevated level of necrosis, a slower rate of healing, and/or a greater recovery period.

Consequently, it would be advantageous to provide a surgical fastener applying apparatus capable of limiting the flow of blood in the tissue immediately adjacent the cut-line to effectuate hemostasis and wound closure, while maximizing blood flow in the surrounding tissue to facilitate healing. Additionally, when tissue is clamped and compressed between the anvil and cartridge, some of the fluid retained within the tissue is squeezed out, which results in greater compression at the portions of the cartridge and the anvil adjacent the cut-line when compared to the lateral edges. It may also be desirable to cut and fasten across tissue that varies in thickness. It would therefore be advantageous to provide fasteners and surgical fastener applying apparatus that are better adapted to apply variable compressive forces to tissue in the interests of addressing these concerns.

SUMMARY

The present disclosure relates to surgical fastener applying apparatus that apply variable compression to tissue, and/or accommodate tissue of varying thickness. More specifically, surgical fastener applying apparatus in accordance with the principles of the present disclosure act to limit the flow of blood through tissue immediately adjacent a cut-line formed therein to effectuate hemostasis, while maximizing the flow of blood through tissue more removed from the cut-line to limit unnecessary necrosis.

In one aspect of the present disclosure, a surgical fastener applying apparatus is disclosed that includes an anvil member having a tissue contacting surface, a surgical fastener cartridge, or cartridge member, that is movably coupled to the anvil member, and a sled.

The cartridge member extends along a longitudinal axis, and is movably coupled to the anvil member. The cartridge member includes a plurality of surgical fasteners and a plurality of pushers that are operatively associated with the plurality of surgical fasteners. Each pusher includes a base portion and a plurality of pusher plates that extend from the base portion such that adjacent pusher plates define an acute angle therebetween.

The aforementioned sled is operably engagable with the plurality of pushers such that engagement of the sled with the pushers urges the surgical fasteners towards the anvil member such that a first row of surgical fasteners applies a first compressive force to tissue disposed between the anvil member and the cartridge member, and a second row of surgical fasteners applies a second, different compressive force to the tissue disposed between the anvil member and the cartridge member.

The pushers and the surgical fasteners may be configured and dimensioned such that the compressive forces are varied along an axis that is transverse to the longitudinal axis of the cartridge member. Additionally, or alternatively, the pushers and the surgical fasteners may be configured and dimensioned such that the compressive forces applied to the tissue decrease outwardly relative to a centerline of the cartridge member such that blood flow through the tissue nearer to the centerline of the cartridge member is less than blood flow through the tissue further from the centerline of the cartridge member.

Each pusher plate extends from the base portion to define a different length. For example, the pusher plates positioned nearer to a centerline of the cartridge member may be shorter than those positioned further from the centerline.

In one embodiment of the surgical fastener applying apparatus, the plurality of pusher plates includes a first pusher plate, a second pusher plate, and a third pusher plate. In this embodiment, the first pusher plate is positioned nearest to the centerline of the cartridge member, the second pusher plate is positioned outwardly of the first pusher plate and further from the centerline, and the third pusher plate is positioned outwardly of the second pusher plate and furthest from the centerline. The first pusher plate extends from the base portion to define a first length, the second pusher plate extends from the base portion to define a second length, and the third pusher plate extends from the base portion to define a third length, wherein the third length is greater than the second length, and the second length is greater than the first length.

The pusher plates are connected to the base portion at a hinge member, e.g., a living hinge. The hinge member is configured to allow the pusher plates to diverge as the pushers are driven towards the anvil member by the sled such that the angles described between adjacent pusher plates are increased.

The disclosed cartridge member includes a top wall having a plurality of retention slots formed therein that are configured and dimensioned to allow the surgical fasteners to pass therethrough during ejection from the cartridge member. Each fastener retention slot is aligned with a corresponding pocket formed in the tissue contacting surface of the anvil member. The fastener pockets formed in the tissue contacting surface of the anvil member may be arranged such that each fastener retention slot is aligned with a plurality of corresponding fastener pockets to reduce any likelihood of improper surgical fastener formation. In one embodiment, it is contemplated that the anvil member may be formed from a plurality of plates that are secured together.

The surgical fasteners are positioned within the cartridge member to define a predetermined distance between penetrating tips thereof and the corresponding pocket formed in the tissue contacting surface of the anvil member. The surgical fasteners positioned nearer to a centerline of the cartridge member may be shorter than the surgical fasteners positioned further from the centerline such that the distance defined between the penetrating tips of the surgical fasteners and the corresponding pockets formed in the tissue contacting surface of the anvil member varies with the distance between the surgical fasteners and the centerline of the cartridge member. For example, it is envisioned that the distance defined between the penetrating tips of the surgical fasteners and the corresponding pockets formed in the tissue contacting surface of the anvil member may increase with the distance between the surgical fasteners and the centerline of the cartridge member.

In one embodiment of the surgical fastener applying apparatus, the plurality of surgical fasteners includes a plurality of first surgical fasteners that are arranged into first rows, second rows, and third rows. In this embodiment, the first rows are positioned nearer to a centerline of the cartridge member, the second rows are positioned outwardly of the first rows and further from the centerline, and the third rows are positioned outwardly of the second rows and furthest from the centerline.

In another aspect of the present disclosure, a surgical fastener applying apparatus is disclosed that includes an anvil member, a cartridge member extending along a longitudinal axis that is movably coupled to the anvil member and configured and dimensioned to retain a plurality of surgical fasteners therein, and one or more pushers that are movably positioned within the cartridge member to eject the plurality of surgical fasteners from the cartridge member into the anvil member to effectuate formation of the plurality of surgical fasteners such that at least two different compressive forces are applied to tissue.

The at least one pusher includes a base portion and a plurality of pusher plates that are connected to the base portion such that the plurality of pusher plates are repositionable relative to a centerline of the cartridge member during movement of the at least one pusher. In one embodiment, it is envisioned that the pusher plates may extend from the base portion such that adjacent pusher plates define an acute angle therebetween. Additionally, or alternatively, it is envisioned that the pusher(s) may be of unitary construction, and/or that each pusher plate may extend from the base portion to define a different length.

Additionally, it is envisioned that the pusher(s) and the surgical fasteners may be configured and dimensioned such that the compressive forces applied to the tissue are varied along an axis that is transverse to the longitudinal axis of the cartridge member.

These and other features of the surgical access apparatus disclosed herein will become more readily apparent to those skilled in the art through reference to the detailed description of various embodiments of the present disclosure that follows.

BRIEF DESCRIPTION OF THE DRAWINGS

Various embodiments of the present disclosure are described hereinbelow with references to the drawings, wherein.

DETAILED DESCRIPTION OF THE EMBODIMENTS

Figure 1:
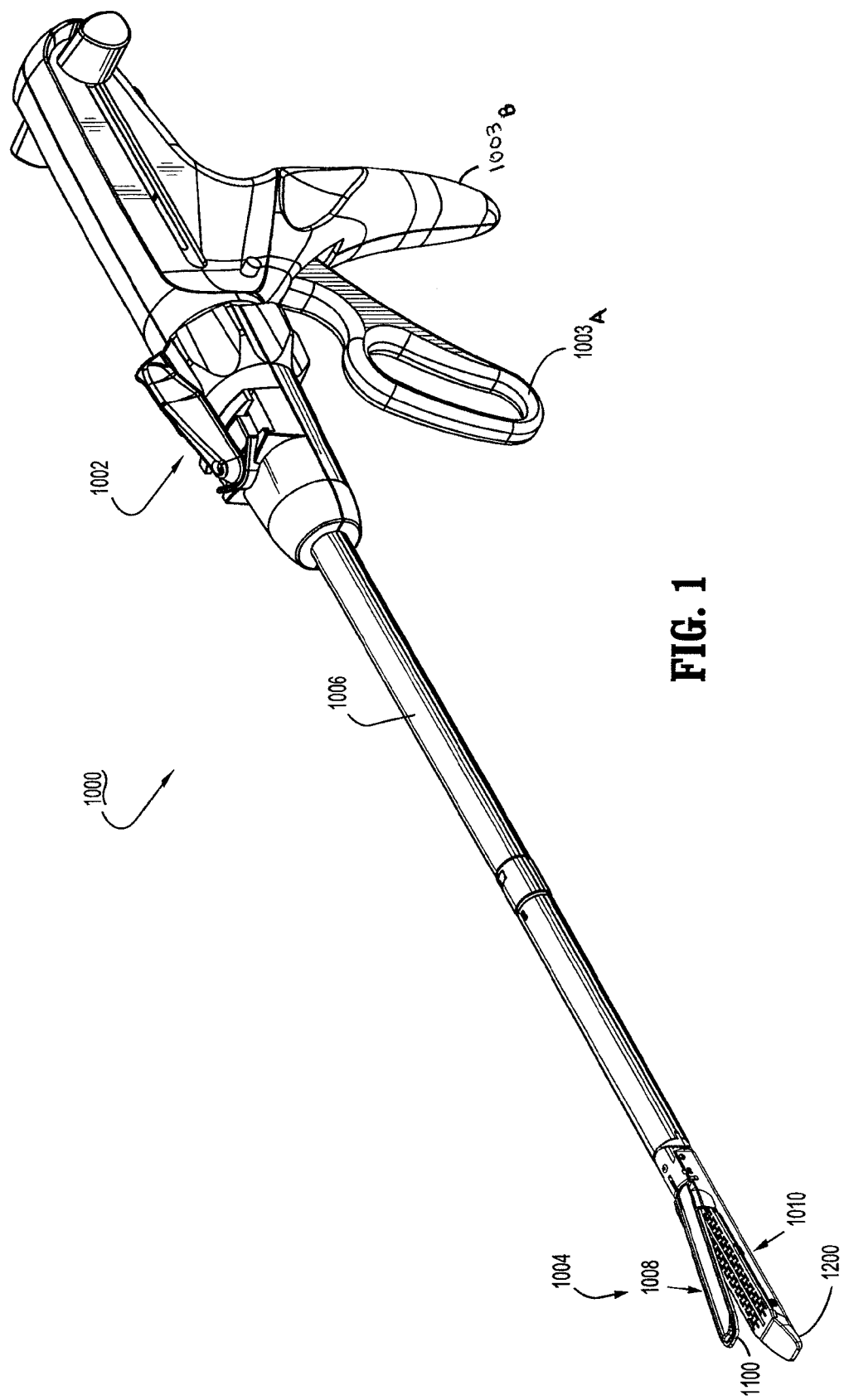
FIG. 1 is a top, perspective view of a surgical fastener applying apparatus having a tool assembly at a distal end thereof for applying a plurality of surgical fasteners to tissue, according to one embodiment of the present disclosure.

Various embodiments of the presently disclosed surgical fastener applying apparatus, and methods of using the same, will now be described in detail with reference to the drawings wherein like references characters identify similar or identical elements. In the drawings, and in the description which follows, the term "proximal" will refer to the end the surgical fastener applying apparatus, or component thereof, that is closest to the clinician during use, while the term "distal" will refer to the end that is furthest from the clinician, as is traditional and conventional in the art. In addition, the term "surgical fastener" should be understood to include any substantially rigid structure that is suitable for the intended purpose of joining tissue together, including but not being limited to surgical staples, clips, and the like.

FIG. 1 illustrates a surgical fastener applying apparatus 1000, of either the re-usable or disposable variety, including a handle assembly 1002, with a movable handle $1003_A$ and a stationary handle $1003_B$, that is operatively connected to a tool assembly 1004 through a distally extending elongated shaft 1006. In various embodiments, the handle assembly 1002 may be manually operated, and either additionally or alternatively, may include motorized, hydraulic, ratcheting, or other such mechanisms. In general, the tool assembly 1004 is adapted to clamp, fasten together, and sever adjacent tissue segments along a cut-line.

Figure 2:
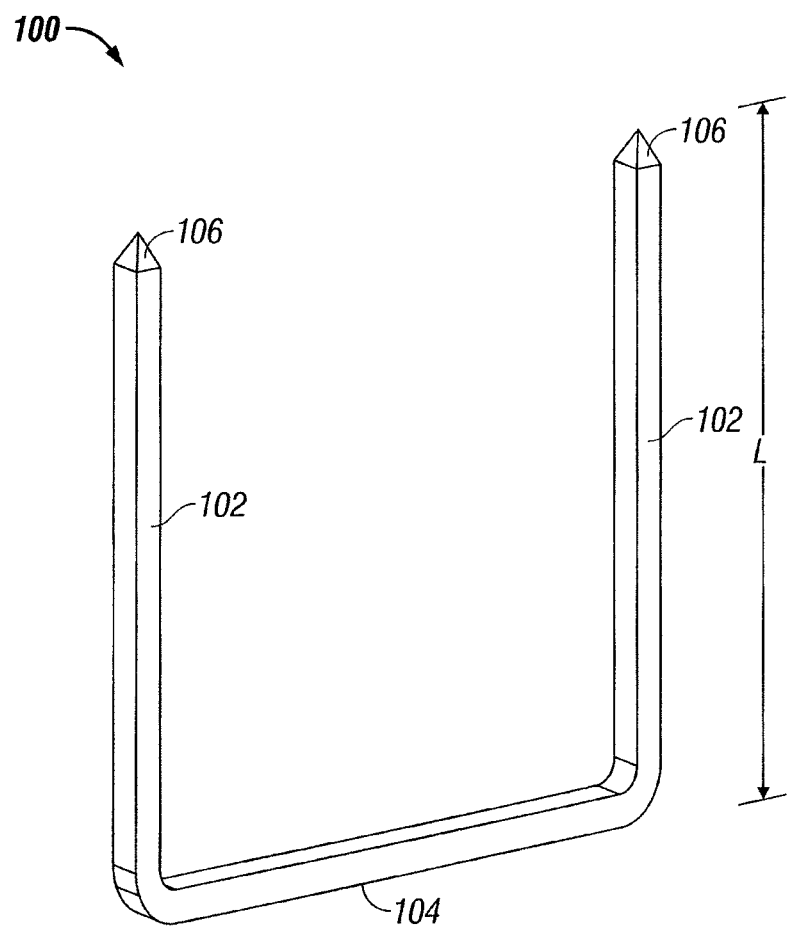
FIG. 2 is a side, perspective view of an exemplary surgical fastener.
Figure 3:
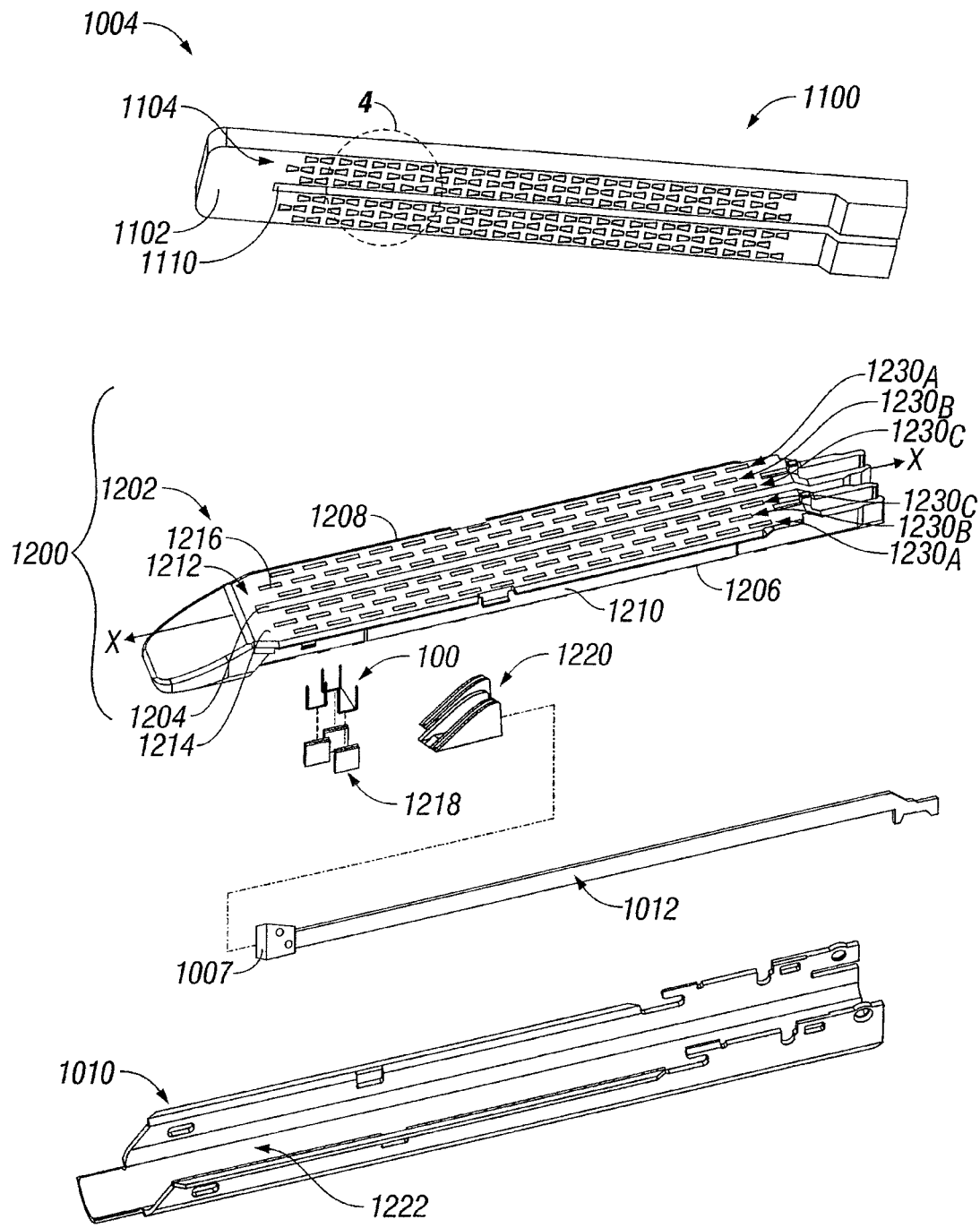
FIG. 3 is a partial, perspective view of the tool assembly seen in FIG. 1, with parts separated, illustrating an anvil and a surgical fastener cartridge assembly including a surgical fastener cartridge incorporating angled pushers.

Referring now to FIGS. 2-6 as well, the tool assembly 1004 includes a first jaw 1008 that is pivotally coupled to a second jaw 1010 to facilitate approximation thereof. The first jaw 1008 of the tool assembly 1004 includes an anvil 1100, and the second jaw 1010 includes a surgical fastener cartridge assembly 1200 that is loaded with a plurality of surgical fasteners 100 (FIGS. 2, 3). Pivoting the movable handle $1003_A$ towards the stationary handle $1003_B$ (FIG. 1) approximates the first jaw 1008 and the second jaw 1010. After the jaws 1008, 1010 are in close operative alignment, continued pivoting of the movable handle $1003_A$ ejects the plurality of surgical fasteners 100 (FIG. 3) from the surgical fastener cartridge assembly 1200 such that the surgical fasteners 100 are driven into the anvil 1100, thus being formed into completed surgical fasteners, as described in further detail below. The tool assembly 1004 and/or the surgical fastener cartridge assembly 1200 may comprise a removable and replaceable loading unit for the surgical fastener applying apparatus 1000.

As best seen in FIG. 2, each surgical fastener 100 includes two legs 102 that are connected by a backspan 104 extending therebetween. The legs 102 extend from the backspan 104 to penetrating ends 106 to define a length "L" prior to formation. The dimensions of the backspan 106 and the legs 102 can be varied such that the surgical fasteners 100 may be used to fasten tissue having varying attributes, e.g., to fasten tissue of varying thickness, and/or to accommodate the presence of scar tissue. The dimensions of the legs 102 and the backspan 104 can be varied such that the surgical fasteners 100 can apply varying amounts of pressure to tissue.

The legs 102 and the backspan 104 may define a cross-section having any suitable geometric configuration including, but not limited to, rectangular, oval, square, triangular, trapezoidal, etc. The legs 102 and the backspan 104 may exhibit the same geometrical configuration, as shown in FIG. 2, or alternatively, the legs 102 and the backspan 104 may exhibit different geometrical configurations. For example, the legs 102 may exhibit a rectangular cross-section, whereas the backspan 104 may exhibit an oval cross-section.

The penetrating ends 106 of the legs 102 may be tapered to facilitate the penetration of tissue, or alternatively, the penetrating ends 106 may not include a taper. In various embodiments, it is also envisioned that the penetrating ends 108, 110 may define either a conical surface, or a flat surface.

Prior to formation, the legs 102 of each surgical fastener 100 may extend from the backspan 104 such that they are substantially parallel. In the alternative, the legs 102 may converge or diverge from the backspan 104.

Referring now to FIG. 3 in particular, the surgical fastener applying apparatus 1000 also includes a knife member 1007 that is operatively connected to a drive beam 1012, as described in commonly assigned U.S. Pat. No. 7,398,908, currently assigned to Tyco Healthcare Group LP, the contents of which are hereby incorporated by reference herein in its entirety, and discussed in further detail below. The knife member 1007 may be configured and dimensioned for simultaneous engagement with both the anvil member 1100 and a cavity 1222 that is defined by the second jaw 1010.

During use, the tool assembly 1004 is first actuated to clamp onto tissue by manipulating the movable handle 1003$_A$ to advance a control rod (not shown) distally. Distal advancement of the control rod results in corresponding movement of the knife member 1007, and effectuates approximation of the anvil member 1100 and the surgical fastener cartridge assembly 1200. With tissue clamped between the anvil member 1100 and the surgical fastener cartridge assembly 1200, the fasteners 100 (FIGS. 2, 3) are fired from the surgical fastener applying apparatus 1000 (FIG. 1) into the tissue. The movable handle 1003$_A$ is then operated again to further advance the knife member 1007.

Figure 4:
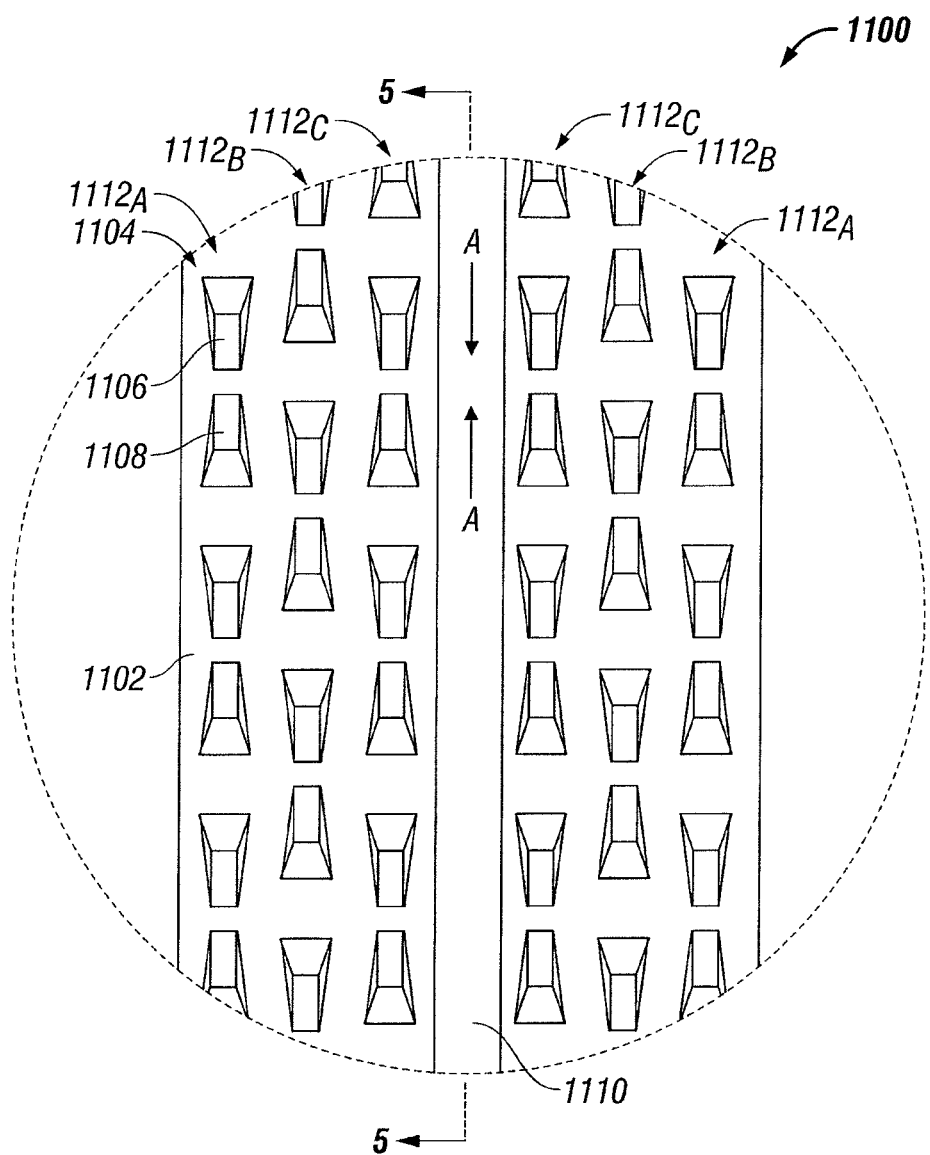
FIG. 4 is a schematic, enlarged view of the area of detail indicated in FIG. 3 illustrating a tissue contacting surface of the anvil and a plurality of fastener pockets formed therein.
Figure 5:
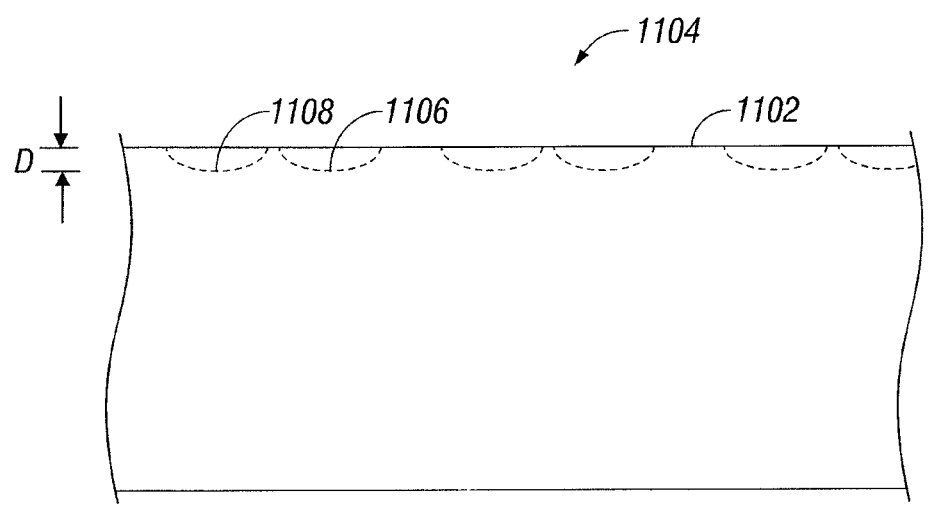
FIG. 5 is a longitudinal, cross-sectional view taken along line 5-5 in FIG. 4 illustrating the fastener pockets formed in the tissue contacting surface of the anvil.
Figure 7:
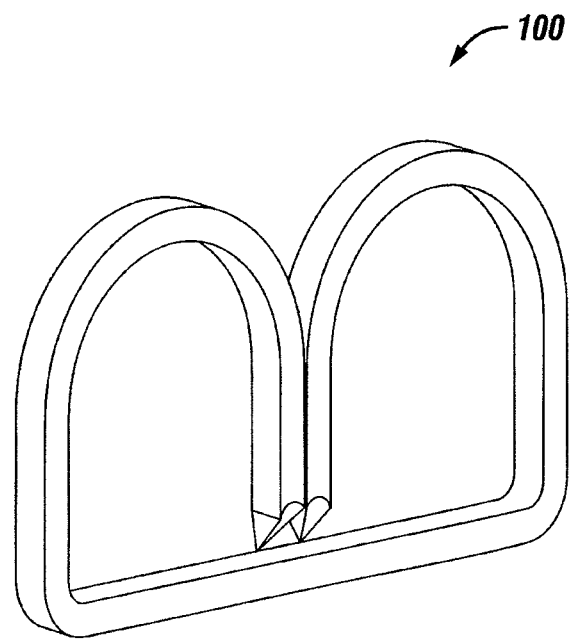
FIG. 7 is a side, perspective view of the surgical fastener shown in FIG. 2 exhibiting a standard "B" shaped configuration subsequent to formation through engagement with the fastener pockets formed in the anvil seen in FIG. 3.
Figure 8:
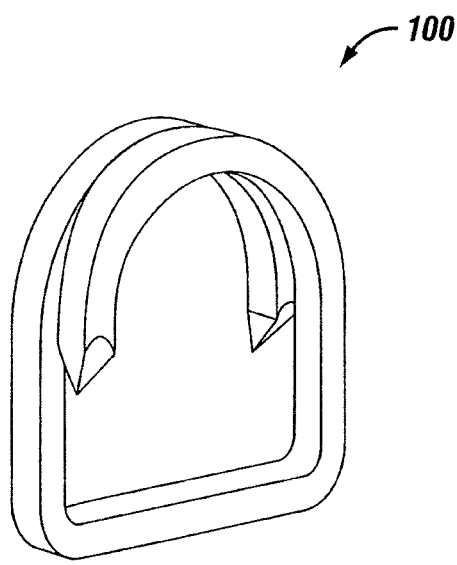
FIG. 8 is side, perspective view of a surgical fastener having a single-loop configuration subsequent to formation through contact with the fastener pockets formed in the tissue contacting surface included in an alternative embodiment of the anvil seen in FIG. 3.

Referring now to FIGS. 3-6, the anvil 1100 and the surgical fastener cartridge assembly 1200 of the tool assembly 1004 (FIG. 1) will be discussed in further detail. The anvil 1100 is an elongated member having a tissue contacting surface 1102 with a plurality of pockets 1104 (FIG. 4) formed therein. Each of the pockets 1104 is positioned to receive the legs 102 (FIG. 2) of the surgical fastener 100, and is configured to redirect the legs 102 to thereby form the surgical fasteners 100. More particularly, in the embodiment of the anvil 1100 seen in FIGS. 3-6, each pocket 1104 includes two forming surfaces 1106, 1108 (FIGS. 4, 5) that extend into the anvil 1100, i.e., away from the tissue contacting surface 1102, to define a depth "D" (FIG. 5). Upon engagement of the legs 102 (FIG. 2) with the forming surfaces 1106, 1108, the forming surfaces 1106, 1108 guide the legs 102 inwardly in the direction of arrows "A" (FIG. 4) to facilitate deformation of the surgical faster 100 into the standard "B" shaped configuration (FIG. 7). In an alternative embodiment, the anvil 1100 may include pockets 1104 that are configured and dimensioned to deform the surgical fastener 100 such that the surgical fastener 100 defines a single-loop configuration (FIG. 8) upon formation. It is also envisioned that the surgical fastener 100 may exhibit other configurations upon formation.

The pockets 1104 are arranged into rows disposed on opposite sides of a slot 1110 extending at least partially through the anvil member 1100 (FIGS. 3, 4). The slot 1110 is configured to accommodate longitudinal movement of the knife member 1007 (FIG. 3) such that tissue may be severed along a cut-line. Although the slot 1110 is depicted as extending longitudinally through the anvil 1100, in alternative embodiments, the slot 1110 may define a configuration that is angled, arcuate, or shaped otherwise. The slot 1110 may extend along a centerline of the anvil 1100, as shown in the embodiment illustrated in FIGS. 3 and 4, or alternatively, the slot 1110 may be spaced therefrom.

Figure 5A:
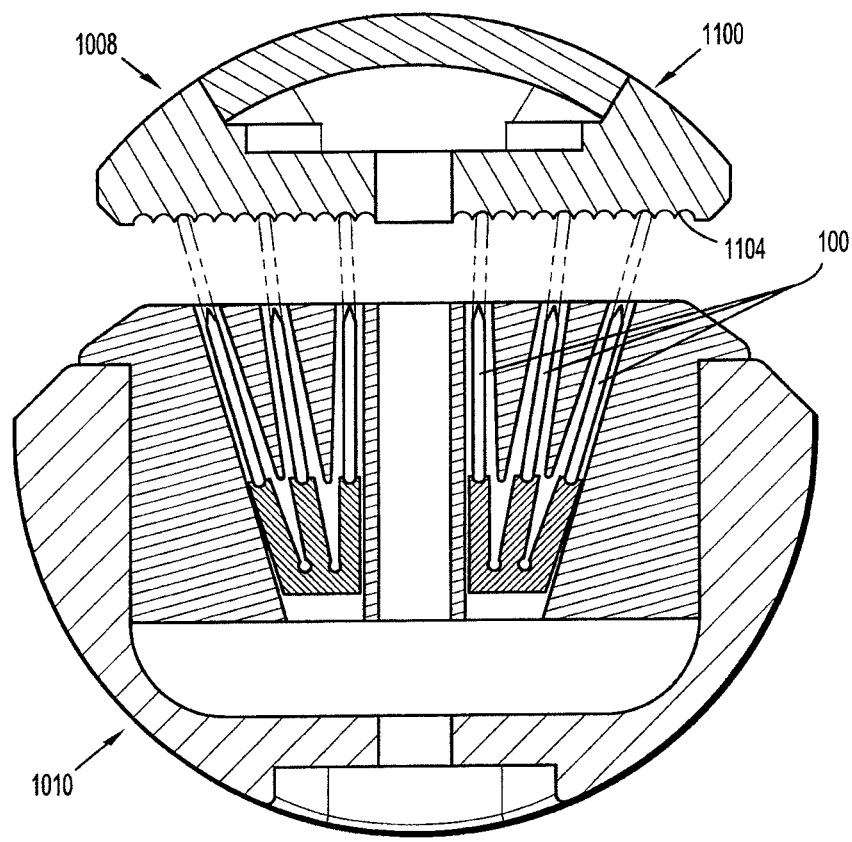
FIG. 5A is a lateral, cross-sectional view of an alternative embodiment of the tool assembly seen in FIG. 1 taken through the fastener pockets formed in the anvil and retention slots formed in the surgical fastener cartridge.

In the specific embodiment of the anvil 1100 seen in FIGS. 3-6, the pockets 1104 are arranged into a pair of outer rows 1112$_A$ (FIG. 4) that are spaced laterally outward of the slot 1110 and furthest therefrom, a pair of intermediate rows 1112$_B$ that are spaced laterally inward of the pair of outer rows 1112$_A$, and a pair of inner rows 1112$_C$ that are spaced laterally inward of the pair of intermediate rows 1112$_B$ and closest to the slot 1110. While the anvil 1100 is depicted as including three rows of pockets 1104, i.e., the respective outer, intermediate, and inner rows 1112$_A$, 1112$_B$, 1112$_C$, the arrangement of pockets 1104 into fewer or greater numbers of rows in alternative embodiments is also within the scope of the present disclosure. With reference to FIG. 5A, in one particular embodiment, the anvil 1100 includes additional rows of pockets 1104 to accommodate for any lateral deflection experienced by the surgical fasteners 100, i.e., towards or away from the slot 1110, as they are deployed through the tissue grasped between the jaws 1008, 1010 (FIG. 1) of the tool assembly 1004. The surgical fasteners 100 may be deflected laterally, for example, due to the presence of scar tissue, irregularities in the tissue, or tissue of increased thickness. By providing additional rows of pockets 1104, the likelihood of engagement between the surgical fasteners 100 and one of the pockets 1104, and thus, proper fastener formation, is increased.

With continued reference to FIGS. 3-6, the surgical fastener cartridge assembly 1200 will be discussed. In the particular embodiment seen in FIGS. 3 and 6, the surgical fastener cartridge assembly 1200 is loaded with three varieties of surgical fastener, i.e., the surgical fasteners 100$_A$, 100$_B$, 100$_C$ seen in FIGS. 9A-11B. In alternative embodiments, however, the surgical fastener cartridge assembly 1200 may include fewer or additional varieties of surgical fasteners 100.

Turning momentarily to FIGS. 9A-11B, it can be seen that the surgical fasteners 100$_A$, 100$_B$, 100$_C$ are substantially identical but for the respective lengths "L$_A$," "L$_B$," "L$_C$" defined by their legs 102$_A$, 102$_B$, 102$_C$. Specifically, the length "L$_B$" defined by the legs 102$_B$ of the surgical fasteners 100$_B$ is less than the length "L$_A$" defined by the legs 102$_A$ of the surgical fasteners 100$_A$, and the length "L$_C$" defined by the legs 102$_C$ of the surgical fasteners 100$_C$ is less than the length "L$_B$" defined by the legs 102$_B$ of the surgical fasteners 100$_B$. Stated differently, the surgical fasteners 100$_C$ have the shortest legs 102$_C$, and the surgical fasteners 100$_A$ have the longest legs 102$_A$.

Figure 6:
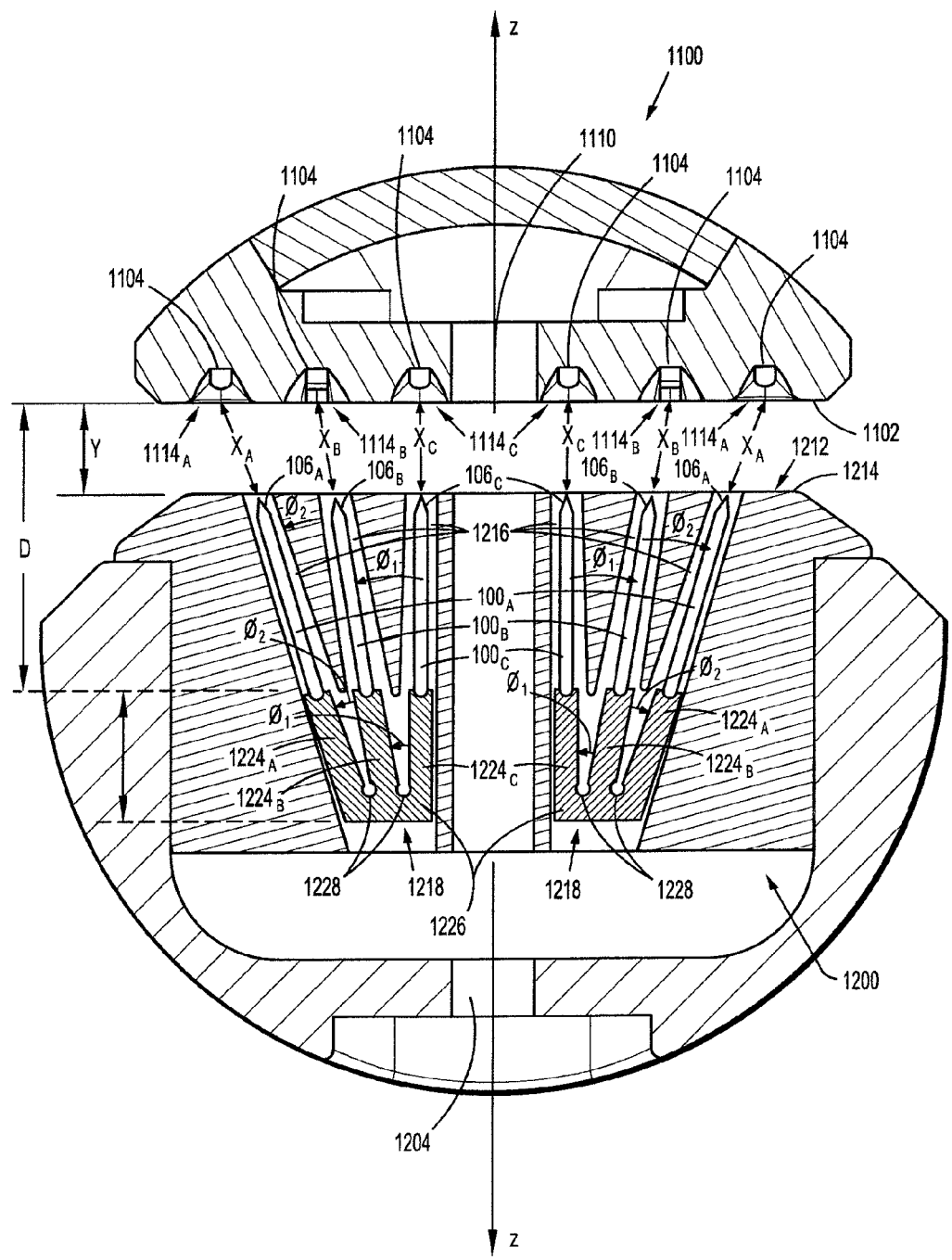
FIG. 6 is a lateral, cross-sectional view of the tool assembly seen in FIG. 1 taken through the fastener pockets formed in the anvil and retention slots formed in the surgical fastener cartridge.

As seen in FIGS. 3 and 6, the surgical fastener cartridge assembly 1200 includes a surgical fastener cartridge body 1202 extending along an axis "X-X" (FIG. 3) that houses, among other components, the surgical fasteners 100$_A$, 100$_B$, 100$_C$ (FIGS. 9A-11B). A longitudinal slot 1204 extends through the surgical fastener cartridge body 1202 that is configured and dimensioned to accommodate longitudinal movement of the knife 1007 (FIG. 3) such that tissue may be severed along the aforementioned cut-line. Although the slot 1204 is depicted as extending longitudinally through the surgical fastener cartridge body 1202, in alternative embodiments, the slot 1204 may define a configuration that is angled, arcuate, or shaped otherwise. The slot 1204 may extend along a centerline of the surgical fastener cartridge body 1202, as shown in the embodiment illustrated in FIGS. 3 and 6, or alternatively, the slot 1204 may be spaced therefrom.

The surgical fastener cartridge body 1202 is defined by a substantially planar bottom wall 1206, a pair of side walls 1208, 1210 that extend upwardly therefrom, and a top wall 1212. The top wall 1212 is also substantially planar, and extends in substantially parallel relation to the bottom wall 1206. The top wall 1212 includes a tissue engaging surface 1214, e.g., for maintaining the position of the tissue to be cut. When the jaws 1008, 1010 (FIG. 1) of the tool assembly 1004 are in an approximated position, the tissue engaging surface 1214 of the top wall 1212 is spaced a distance "Y" (FIG. 6) from the tissue contacting surface 1102 of the anvil 1100.

The tissue engaging surface 1214 of the top wall 1212 further includes a plurality of fastener retention slots 1216 formed therein. Each fastener retention slot 1216 is configured and dimensioned to receive one of the surgical fasteners 100$_A$, 100$_B$, 100$_C$ (FIGS. 6, 9A-11B). To drive the surgical fasteners 100$_A$, 100$_B$, 100$_C$ upwardly, i.e., towards the top wall 1212, and through the fastener retention slots 1216, the surgical fastener cartridge assembly 1200 further includes a plurality of pushers 1218 (FIG. 3) and a sled 1220 that is disposed within the cavity 1222 defined by the second jaw 1010 of the tool assembly 1004 (FIG. 1).

The pushers 1218 are positioned beneath the surgical fasteners 100$_A$, 100$_B$, 100$_C$ and are configured to engage the sled 1220 as the sled 1220 traverses the cavity 1222 via translation of the drive beam 1012, or other such actuation component.

Each pusher 1218 includes a plurality of pusher plates, identified generally by the reference character 1224, corresponding in number to the number of rows of fastener lines desired within the tissue upon firing of the surgical fastener applying apparatus 1000 (FIG. 1). Accordingly, in the embodiment seen in FIGS. 3 and 5, each pusher 1218 includes three pusher plates, i.e., outer, intermediate, and inner pusher plates $1224_A$, $1224_B$, $1224_C$, respectively. In alternative embodiments, however, it is envisioned that the pushers 1218 may include fewer or greater numbers of pusher plates 1224 should the desired number of rows of fastener lines be fewer or greater.

Each of the respective outer, intermediate, and inner pusher plates $1224_A$, $1224_B$, $1224_C$ extends upwardly from, and is connected to, a base portion 1226 of the pusher 1218 at one or more hinge members 1228. In one embodiment, as seen in FIG. 6 for example, the hinge member(s) 1228 may comprise a living hinge formed integrally with the pusher 1218. The hinge member(s) 1228 permit the outer, intermediate, and inner pusher plates $1224_A$, $1224_B$, $1224_C$ to diverge as the pushers 1218 are driven upwardly by the sled 1220 (FIG. 3). The outer, intermediate, and inner pusher plates $1224_A$, $1224_B$, $1224_C$ extend from the base portion 1226 in offset relation such that the outer pusher plate $1224_A$ and the intermediate pusher plate $1224_B$ subtend a first acute angle $\theta_1$, while the intermediate pusher plate $1224_B$ and the outer pusher plate $1224_C$ subtend a second acute angle $\theta_2$.

In one particular embodiment, the pushers 1218 are unitary in construction, as shown in FIG. 6 for example, such that the pusher plates 1224 extend directly from the base portion 1226. For example, it is envisioned that the pusher plates 1224 may be integrally, e.g., monolithically, formed with the base portion 1226. It is also envisioned, however, that the pushers 1218 and the pusher plates 1224 may constitute separate, discrete structures.

The outer, intermediate, and inner pusher plates $1224_A$, $1224_B$, $1224_C$ are configured and dimensioned to engage the surgical fasteners $100_A$, $100_B$, $100_C$, respectively. Consequently, the surgical fasteners $100_A$, $100_B$, $100_C$ are also arranged within the surgical fastener cartridge body 1202 in offset relation such that the surgical fasteners $100_A$, $100_B$ subtend the first acute angle $\theta_1$ and the surgical fasteners $100_B$, $100_C$ subtend the second acute angle $\theta_2$.

The distance "D" measured from the pushers 1218 to the tissue contacting surface 1102 of the anvil 1100 for each of the pushers 1218 is substantially the same. While the height of each pusher 1218, measured along the vertical axis "Z-Z," or height, of the surgical fastener cartridge 1200 is substantially the same, the offset relationship between the respective outer, intermediate, and inner pusher plates $1224_A$, $1224_B$, $1224_C$ results in each pusher plate defining a different length. More specifically, in the embodiment seen in FIG. 6, the outer pusher plate $1224_A$ defines a greater length than the intermediate pusher plate $1224_B$, and the intermediate pusher plate $1224_B$ defines a greater length than the inner pusher plate $1224_C$. Stated differently, the pushers 1218 are arranged beneath the surgical fasteners $100_A$, $100_B$, $100_C$ such that shortest pusher plate, i.e., inner pusher plate $1224_C$, is disposed closest to the slot 1204 and beneath the shortest surgical fastener, i.e., the surgical fastener $100_A$, and the longest pusher plate, i.e., the outer pusher plate $1224_A$, is disposed furthest from the slot 1204 and beneath the longest surgical fastener, i.e., the surgical fasteners $100_C$.

The offset relationship between the respective outer, intermediate, and inner pusher plates $1224_A$, $1224_B$, $1224_C$, and the corresponding offset relationship between the surgical fasteners $100_A$, $100_B$, $100_C$, results in the definition of a variable distance between the respective penetrating ends $106_A$, $106_B$, $106_C$ of the surgical fasteners $100_A$, $100_B$, $100_C$ and the pockets 1104 formed in the tissue contacting surface 1102 of the anvil 1100. More specifically, the penetrating ends $106_A$ of the surgical fasteners $100_A$ are spaced a distance "$X_A$" from the pockets 1104 comprising the pair of outer rows $1112_A$ (FIG. 4), the penetrating ends $106_B$ of the surgical fasteners $100_B$ are spaced a distance "$X_B$" from the pockets 1104 comprising the intermediate pair of rows $1112_B$, and the penetrating ends $106_C$ of the surgical fasteners $100_C$ are spaced a distance "$X_C$" from the pockets 1104 comprising the inner pair of rows $112_C$. In the illustrated embodiment, the distance "$X_A$" is less than the distance "$X_B$," and the distance "$X_B$" is less than the distance "$X_C$."

The fastener retention slots 1216 are arranged into pairs of outer, intermediate, and inner rows $1230_A$, $1230_B$, $1230_C$ (FIG. 3) that correspond respectively to the pairs of outer, intermediate, and inner rows $1112_A$, $1112_B$, $1112_C$ (FIG. 4) of pockets 1104 formed in the tissue contacting surface 1102 of the anvil 1100, thus increasing the likelihood of proper engagement between the surgical fasteners $100_A$, $100_B$, $100_C$ and the pockets 1104. Accordingly, upon ejection of the surgical fasteners $100_A$, $100_B$, $100_C$ from the fastener retention slots 1216, the surgical fasteners $100_A$ are directed into contact with the pockets 1104 comprising the pair of outer rows $1112_A$, the surgical fasteners $100_B$ are directed into contact with the pockets 1104 comprising the pair of intermediate rows $1112_B$, and the surgical fasteners $100_C$ are directed into contact with the pockets 1104 comprising the pair inner of rows $1112_C$. In one embodiment, as seen in FIG. 6, the fastener retention slots 1216 comprising the pairs of outer, intermediate, and inner rows $1230_A$, $1230_B$, $1230_C$ may be connected at lead-ins 1232, which may be radiused, as shown, or of any other suitable configuration, e.g., planar or pointed. Alternatively, however, it is envisioned that the fastener retention slots 1216 comprising the respective outer, intermediate, and inner pairs of rows $1230_A$, $1230_B$, $1230_C$ may be discrete.

The pair of outer rows $1230_A$ (FIGS. 3, 6) of fastener retention slots 1216 are spaced laterally outward of the slot 1204 and are disposed furthest therefrom, the pair of intermediate rows $1230_B$ are spaced inwardly of the pair of outer rows $1230_A$, and the pair of inner rows $1230_C$ are spaced inwardly of the pair of intermediate rows $1230_B$ and are disposed closest to the slot 1204, each of the respective inner, intermediate, and outer pairs of rows $1230_A$, $1230_B$, $1230_C$ being arranged on opposite sides of the slot 1204. Consequently, as the surgical fasteners $100_A$, $100_B$, $100_C$ exit the fastener retention slots 1216 and are formed within tissue, the surgical fasteners $100_A$, $100_B$, $100_C$ will be arranged to respectively define outer, intermediate, and inner fastener lines on opposite sides of the cut-line formed in the tissue. While the surgical fastener cartridge body 1202 is depicted as including three pairs of rows, i.e., the respective outer, intermediate, and inner rows $1230_A$, $1230_B$, $1230_C$, fewer and greater numbers of rows of fastener retention slots 1216 may be included in alternative embodiments of the surgical fastener cartridge assembly 1200.

Figure 9A:
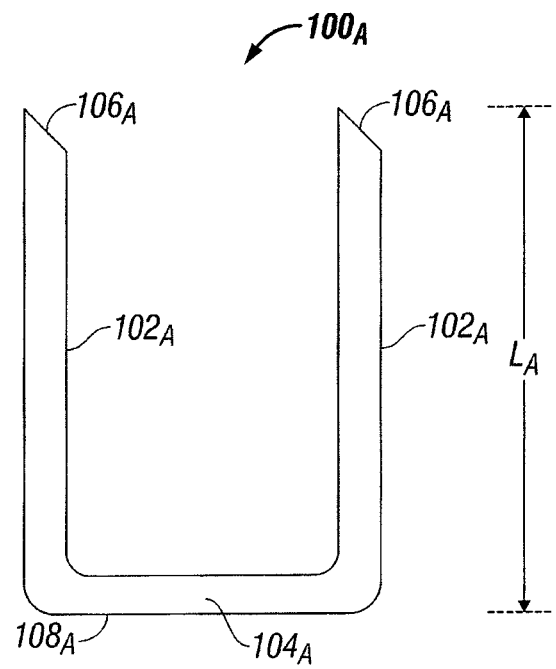
FIG. 9A is a side, plan view of one embodiment of the surgical fastener shown in FIG. 2 including legs having a first length and shown prior to formation.
Figure 9B:
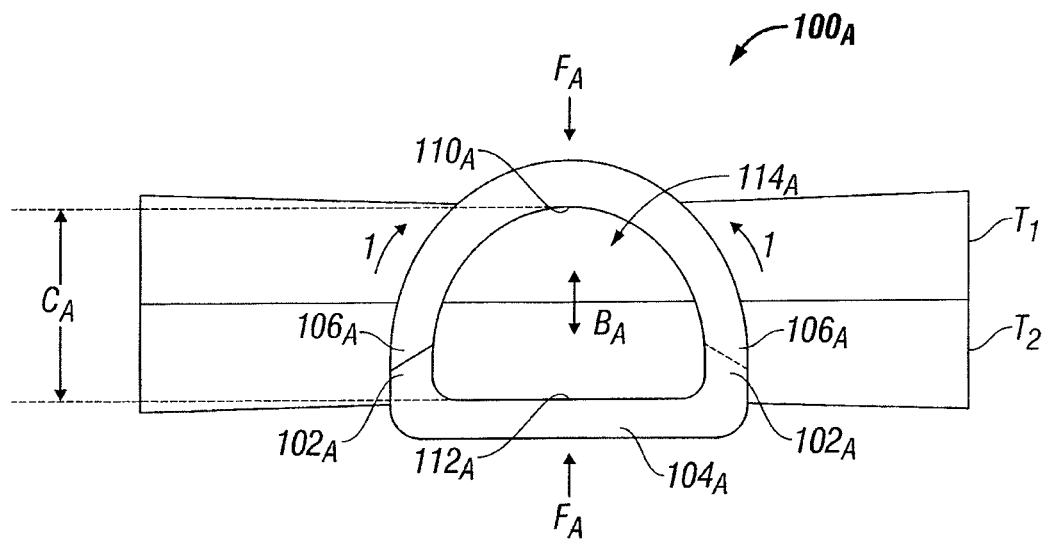
FIG. 9B is a cross-sectional view of the surgical fastener shown in FIG. 9A subsequent to formation within adjacent tissue segments to apply a first compressive force thereto.

With reference again to FIGS. 9A-9B, the surgical fasteners $100_A$ will be discussed before and after formation. As seen in FIG. 9A, before formation, the legs $102_A$ of the surgical fastener $100_A$ define a length "$L_A$" that is measured from the penetrating ends $106_A$ to an outer surface $108_A$ of the backspan $104_A$. After formation, the legs $102_A$ are configured such that the surgical fastener $100_A$ defines, for example, the standard "B" shaped configuration (FIG. 9B). When formed within adjacent tissue segments "$T_1$" "$T_2$," the tissue segments "$T_1$" "$T_2$" are compressed and maintained in approximation between an inner surface $110_A$ of the curved legs $102_A$ and an inner surface $112_A$ of the backspan $104_A$ within a compressive space $114_A$. The compression of the tissue segments "$T_1$" "$T_2$" creates a biasing force "$B_A$" in the tissue segments "$T_1$" "$T_2$" that endeavors to force the legs $102_A$ of the surgical fastener $100_A$ outwardly in the direction indicated by arrows 1. The legs $102_A$ resist yielding, but their length "$L_A$" allows the legs $102_A$ to be deflected outwardly, albeit a minimal distance, under the influence of the biasing force "$B_A$" such that the compressive space $114_A$ ultimately defines a dimension "$C_A$." Maintaining the tissue segments "$T_1$," "$T_2$" within the compressive space $114_A$ subjects the tissue segments "$T_1$" "$T_2$" to a corresponding compressive force "$F_A$" which limits, but does not completely restrict, the flow of blood through the tissue surrounding the surgical fastener $100_A$. Thus, unnecessary necrosing of the fastened tissue segments "$T_1$" "$T_2$" may be prevented or impeded.

Figure 10A:
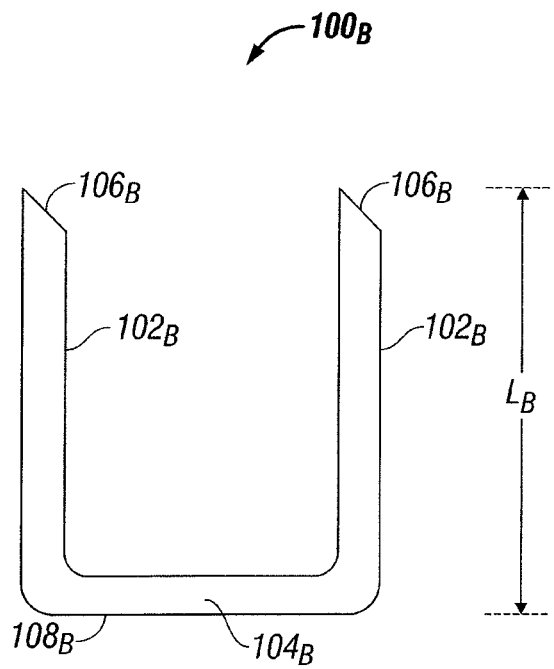
FIG. 10A is a side view of another embodiment of the surgical fastener shown in FIG. 2 including legs having a second, shorter length and shown prior to formation.
Figure 10B:
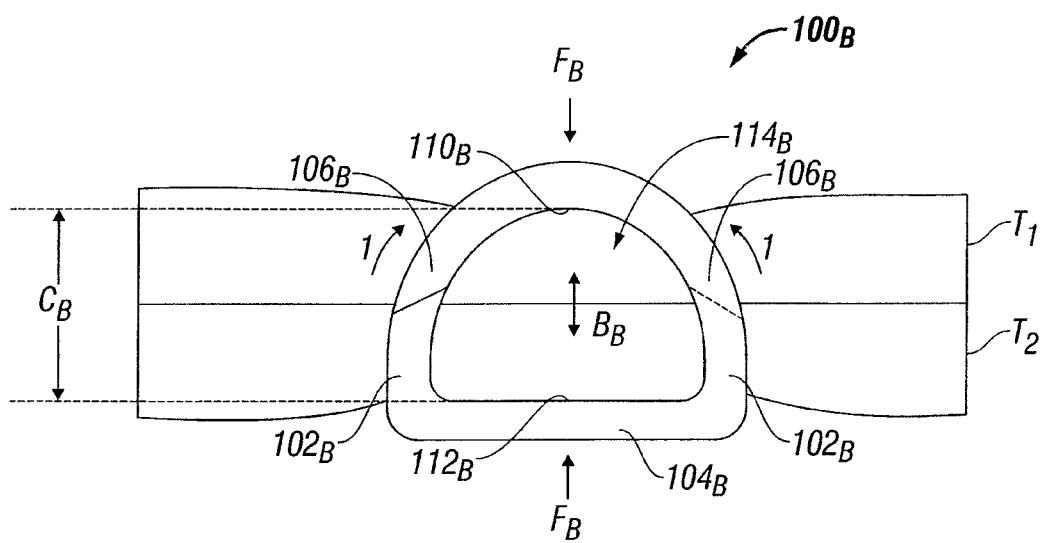
FIG. 10B is a cross-sectional view of the surgical fastener shown in FIG. 10A subsequent to formation within adjacent tissue segments to apply a second, greater compressive force thereto.

With reference now to FIGS. 10A-10B, the surgical fastener $100_B$ is shown before and after formation, respectively. Before formation, the legs $102_B$ define a length "$L_B$" that is measured from the penetrating ends $106_B$ to the outer surface $108_B$ of the backspan $104_b$. The length "$L_B$" is less than the length "$L_A$" defined by the legs $102_A$ of the surgical fastener $100_A$ illustrated in FIGS. 9A-9B. After formation, the legs $102_B$ are configured such that the surgical fastener $100_B$ also defines the standard "B" shaped configuration (FIG. 10B). When the surgical fastener $100_B$ is formed within tissue segments "$T_1$" "$T_2$," the compressed tissue segments "$T_1$," "$T_2$" exert a biasing force "$B_B$" that endeavors to force the legs $102_B$ outwardly in the direction indicated by arrows 1. The shorter length "$L_B$" of the legs $102_B$ allows the legs $102_B$ to resist yielding to a greater extent than the legs $102_A$ of the surgical fastener $100_A$ such that a compressive space $114_B$ is ultimately defined with a dimension "$C_B$" that is smaller in comparison to the dimension "$C_A$" of the compressive space $114_A$ illustrated in FIG. 9B. The smaller dimension "$C_B$" of the compressive space $114_B$ results in the application of a corresponding compressive force "$F_B$" to the tissue segments "$T_1$" "$T_2$" that is greater than the compressive force "$F_A$" applied by the surgical fastener $100_A$. Consequently, the flow of blood through the tissue surrounding the surgical fastener $100_B$ is further restricted when compared to the flow of blood through the tissue surrounding the surgical fastener $100_A$, thereby further facilitating hemostasis. The compressive force "$F_B$" does not completely restrict the flow of blood through the tissue surrounding the surgical fastener $100_B$, however. Thus, unnecessary necrosing of the fastened tissue segments "$T_1$" "$T_2$" may be prevented or impeded.

Figure 11A:
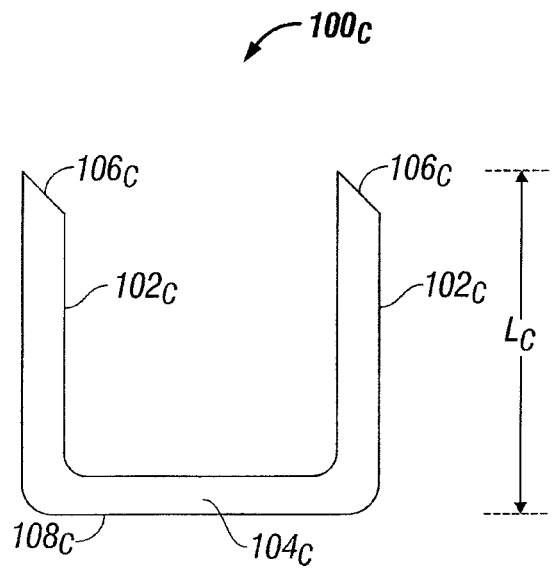
FIG. 11A is a side view of still another embodiment of the surgical fastener shown in FIG. 2 including legs having a third, shorter length and shown prior to formation.
Figure 11B:
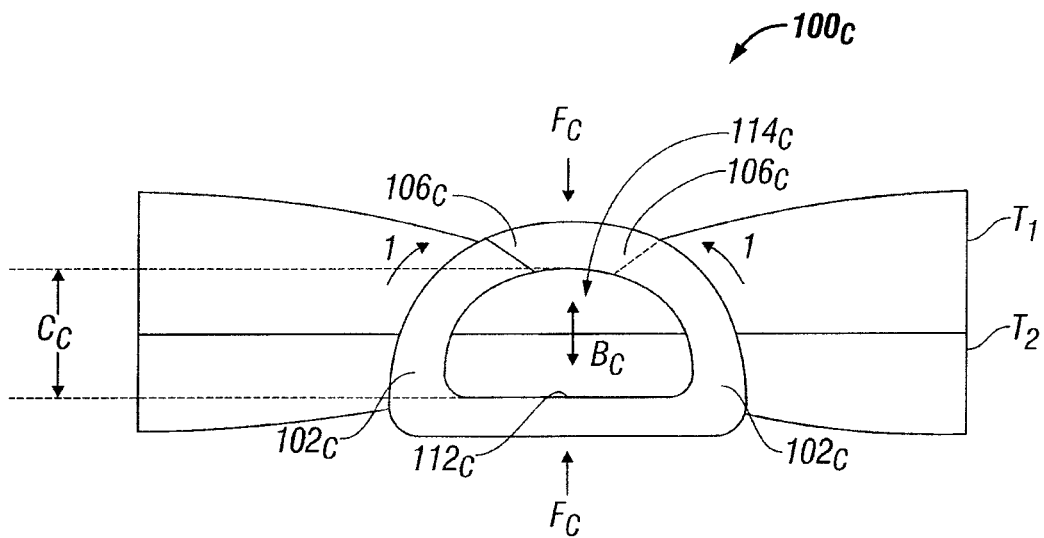
FIG. 11B is a cross-sectional view of the surgical fastener shown in FIG. 11A subsequent to formation within adjacent tissue segments to apply a third, greater compressive force thereto.

FIGS. 11A-11B illustrate the surgical fastener $100_C$ before and after formation, respectively. Before formation, the legs $102_C$ define a length "$L_C$" that is measured from the penetrating ends $106_C$ to the outer surface $108_C$ of the backspan $104_C$. The length "$L_C$" is less than the length "$L_B$" defined by the legs $102_B$ of the surgical fastener $100_B$ illustrated in FIGS. 10A-10B. After formation, the legs $102_C$ are configured such that the surgical fastener $100_C$ also defines the standard "B" shaped configuration (FIG. 11B). When the surgical fastener $100_C$ is formed within tissue segments "$T_1$" "$T_2$," the compressed tissue segments "$T_1$" "$T_2$" exert a biasing force "$B_C$" that endeavors to force the legs $102_C$ outwardly in the direction indicated by arrows 1. The shorter length "$L_C$" of the legs $102_C$ allows the legs $102_C$ to resist yielding to a greater extent than the legs the legs $102_B$ of the surgical fastener $100_B$ such that a compressive space $114_C$ is ultimately defined with a dimension "$C_C$" that is smaller in comparison to the dimension "$C_B$" of the compressive space $114_B$ illustrated in FIG. 10B. The smaller dimension "$C_C$" of the compressive space $114_C$ results in the application of a corresponding compressive force "$F_C$" to the tissue segments "$T_1$" "$T_2$" that is greater than the compressive force "$F_B$" applied by the surgical fastener $100_B$. Consequently, the flow of blood through the tissue surrounding the surgical fastener $100_C$ is further restricted when compared to the flow of blood through the tissue surrounding the surgical fastener $100_B$. The compressive force "$F_C$" applied to the tissue segments "$T_1$" "$T_2$" substantially, if not completely restricts the flow of blood through the tissue surrounding the surgical fastener $100_C$, thereby further facilitating, and effectuating hemostasis.

The length "$L_A$" of the legs $102_A$, the length "$L_B$" of the legs $102_B$, and the length "$L_C$" of the legs $102_C$, as well as the corresponding dimensions "$C_A$," "$C_B$," "$C_C$" of the compressive spaces $114_A$, $114_B$, $114_C$ occupied by tissue segments "$T_1$" "$T_2$" when the respective surgical fasteners $100_A$, $100_B$, $100_C$ are in their formed conditions, may be altered or varied in different embodiments of the present disclosure to effectuate any desired level of hemostasis and blood flow in the tissue segments "$T_1$" "$T_2$." Furthermore, the size of the surgical fasteners $100_A$, $100_B$, $100_C$ may be substantially the same, or may vary within a row of retention slots 1216, or in any other pattern.

Figure 12:
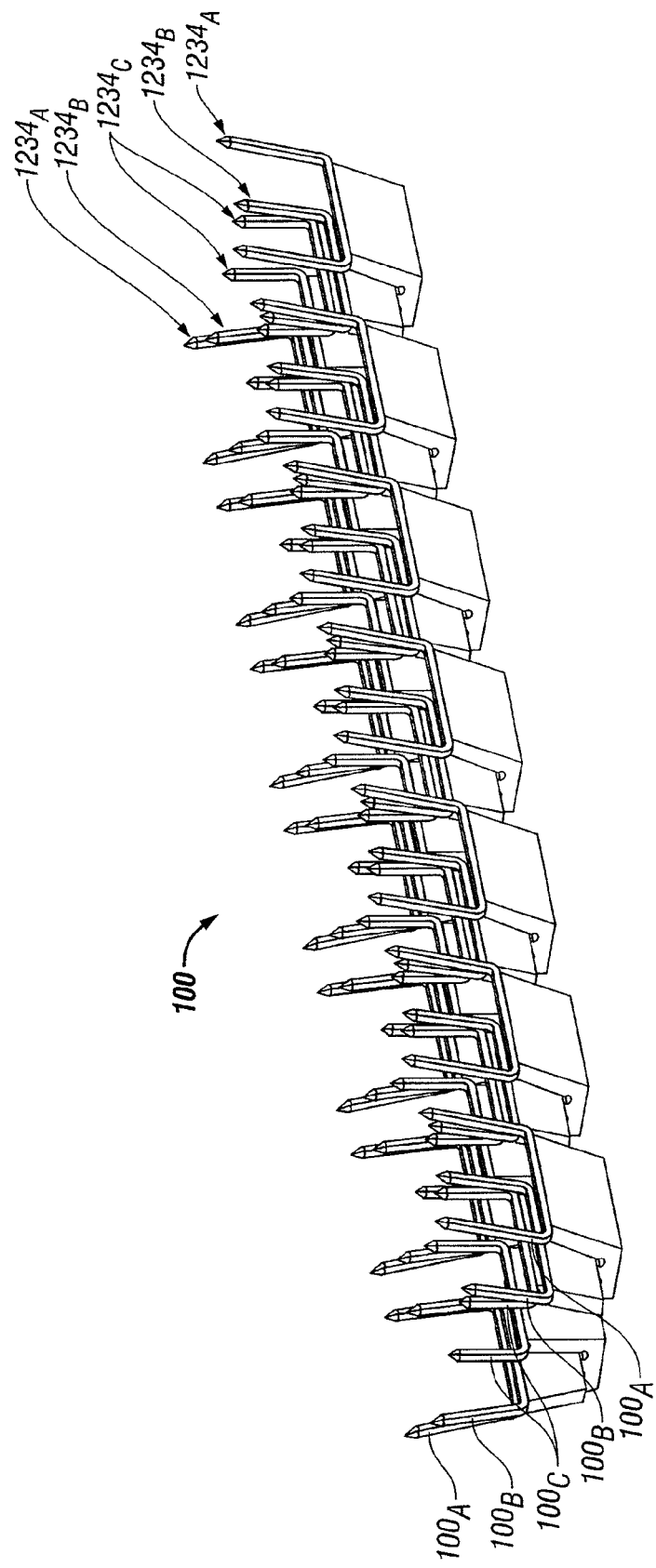
FIG. 12 is a partial, longitudinal, perspective view, with parts removed, of the surgical fastener cartridge seen in FIG. 3 illustrating the plurality of surgical fasteners arranged into inner, intermediate, and outer rows.
Figure 13:
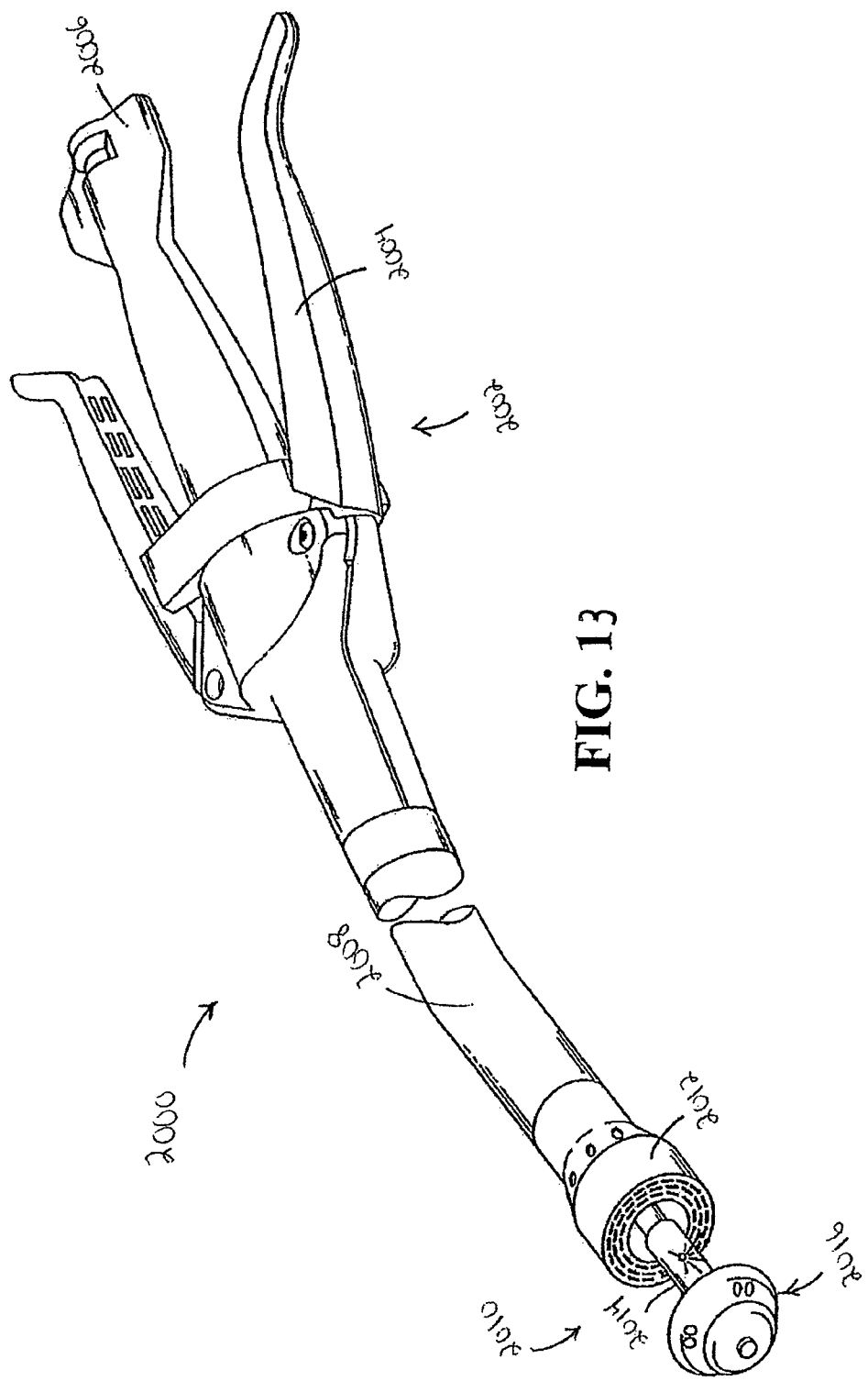
FIG. 13 illustrates an end-to-end anastomosis device for use with alternative embodiments of the anvil and the surgical fastener cartridge seen in FIG. 3.
Figure 14:
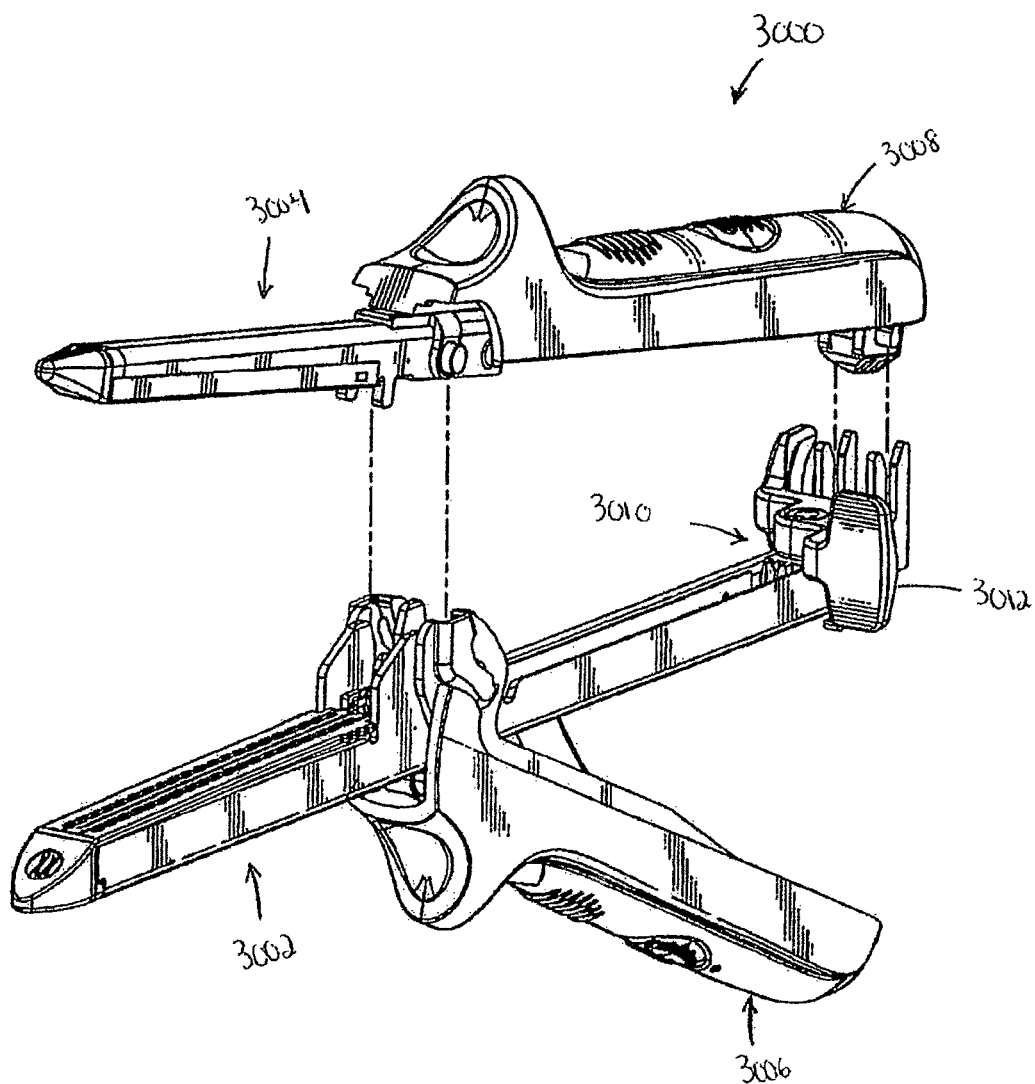
FIG. 14 illustrates a surgical fastener applying instrument for use with alternative embodiments of the anvil and the surgical fastener cartridge seen in FIG. 3.
Figure 15:
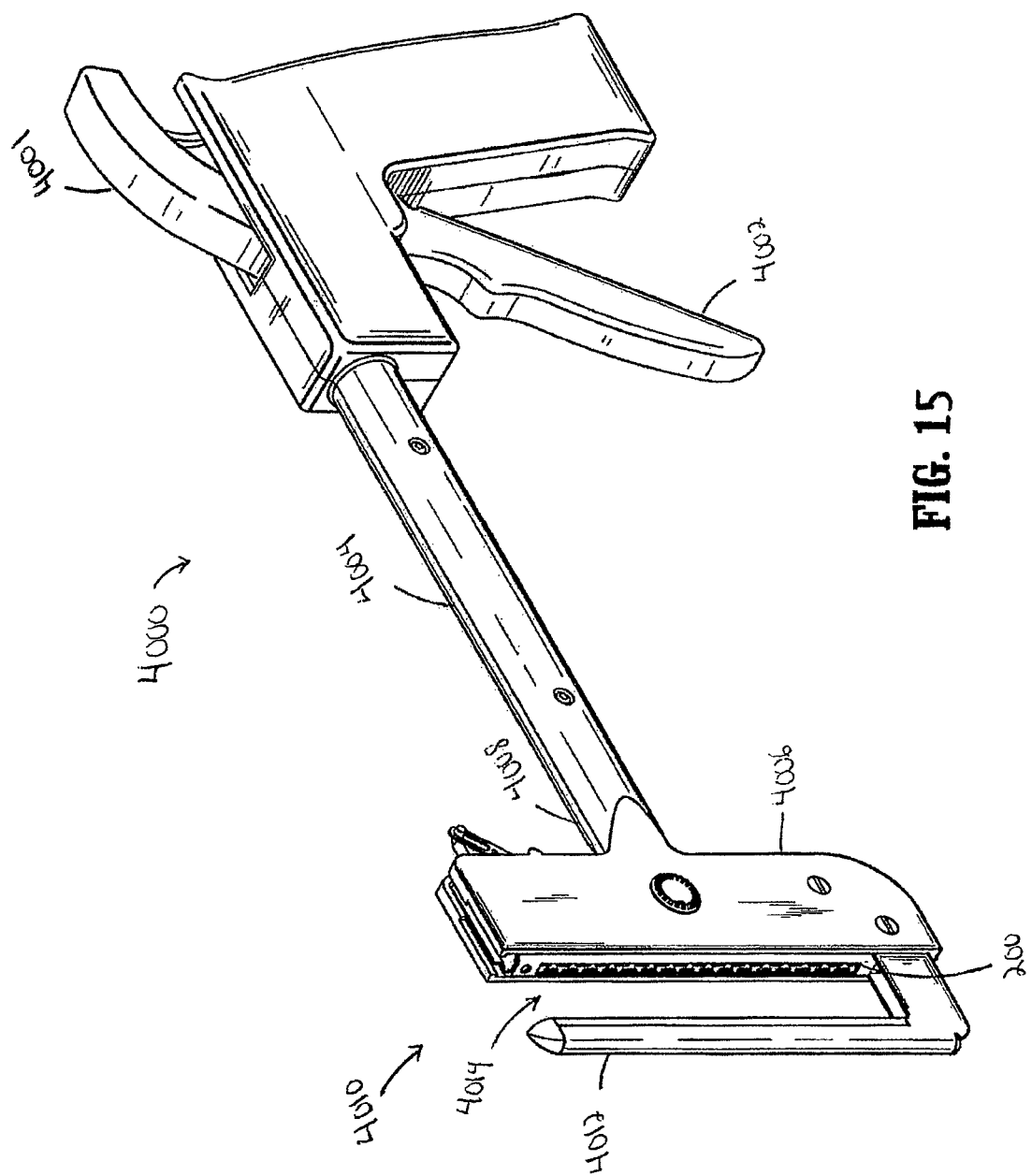
FIG. 15 illustrates a transverse anastomosis fastener applying instrument for use with alternative embodiments of the anvil and the surgical fastener cartridge seen in FIG. 3.

Referring now to FIGS. 6 and 12, the pushers 1218 are arranged longitudinally on opposite sides of the slot 1204 extending through the surgical fastener cartridge body 1202 such that the surgical fasteners $100_A$, $100_B$, $100_C$ define pairs of outer, intermediate, and inner rows $1234_A$, $1234_B$, $1234_C$ that correspond respectively in position to the outer, intermediate, and inner rows $1230_A$, $1230_B$, $1230_C$ (FIG. 3) of fastener retention slots 1216. Accordingly, the surgical fasteners $100_A$ comprising the pair of outer rows $1234_A$ will be spaced laterally outward, and furthest from, the cut-line formed upon fastening, the surgical fasteners $100_B$ comprising the pair of intermediate rows $1234_B$ will be disposed inwardly of the surgical fasteners $100_A$ comprising the pair of outer rows $1234_A$, and the fasteners $100_C$ comprising the pair of inner rows $1234_C$ will be disposed inwardly of the surgical fasteners $100_B$ comprising the pair of intermediate rows $1234_B$, along the cut-line, and closest thereto. The respective outer, intermediate, and inner rows $1234_A$, $1234_B$, $1234_C$ of surgical fasteners $100_A$, $100_B$, $100_C$ will be applied to the tissue such that they define corresponding lines of fasteners on opposite sides of the cut-line.

The surgical fastener cartridge body 1202 seen in FIGS. 3, 6, and 12 is illustrated as including outer, intermediate, and inner rows $1234_A$, $1234_B$, $1234_C$ exclusively including the respective surgical fasteners $100_A$, $100_B$, $100_C$. In other words, each surgical fastener disposed in a particular row will have the same configuration, i.e., legs of the same length. By arranging the surgical fasteners $100_A$, $100_B$, $100_C$ in this manner, the surgical fasteners with the shortest leg length resulting in the greatest compressive force, i.e., surgical fasteners $100_C$, are deployed closest to the cut-line, and the surgical fasteners having longer legs and resulting in lesser compressive forces, i.e., surgical fasteners $100_A$ and $100_B$, are provided further from the cut-line. Consequently, arranging the surgical fasteners $100_A$, $100_B$, $100_C$ in this way minimizes the flow of blood through the tissue immediately adjacent the cut-line and gradually increases the flow of blood through the tissue spaced a greater lateral distance therefrom. It should be appreciated that the length of the legs could be varied to accommodate tissue of different thicknesses and to control tissue compression by the fasteners $100_A$, $100_B$, $100_C$.

In alternative embodiments of the present disclosure, it is envisioned that the surgical fastener cartridge body 1202 may include outer, intermediate, and inner rows $1234_A$, $1234_B$, $1234_C$ comprising a combination of surgical fasteners $100_A$, $100_B$, $100_C$ such that a particular row may include a variety of surgical fasteners having different configurations, e.g., legs of different lengths. By providing a variety of surgical fasteners in each row, the flow of blood through the tissue can be controlled longitudinally, along the cut-line, as well laterally as the distance therefrom is varied.

With continued reference to FIG. 12, by loading the surgical fastener cartridge 1200 (FIG. 3) with a variety of surgical fasteners, e.g., surgical fasteners $100_A$, $100_B$, $100_C$, and by arranging the surgical fasteners $100_A$, $100_B$, $100_C$ such that those with the shortest legs, i.e., surgical fasteners $100_C$, are closest to the cut-line and those with the longest legs, i.e., surgical fasteners $100_A$, are furthest from the cut-line, a greater range of tissue thickness can be effectively fastened, as the thickness of the tissue will generally increase with the distance from the cut-line, e.g., as a result of clamping by the tool assembly 1004 (FIG. 1). Accordingly, loading the surgical fastener cartridge 1200 with a variety of surgical fasteners having legs of various lengths allows a single surgical fastener cartridge 1200 to fasten tissue of varying thickness.

Referring now to FIGS. 1-6 and 9-12, a method of fastening tissue with the surgical fastener applying apparatus 1000 (FIG. 1) will be discussed. During use, the surgical fastener applying apparatus 1000 is approximated and fired similarly to, and in accordance with other known surgical fastener applying apparatus, such as that disclosed in commonly assigned U.S. Pat. No. 5,865,361, currently assigned to Tyco Healthcare Group LP, the contents of which are hereby incorporated by reference herein in its entirety.

The movable handle $1003_A$ is operatively connected to an actuation shaft, which receives the proximal end of a control rod, such that manipulation of the movable handle $1003_A$ results in linear advancement of the actuation shaft, which causes corresponding linear advancement of the control rod. An axial drive assembly is also provided that is engagable with the control rod. More specifically, the axial drive assembly includes the elongated drive beam 1012 (FIG. 3), which includes a distal end that supports the knife blade 1007, and a drive member that is configured and dimensioned for engagement with the control rod. As seen in FIG. 3, the knife 1007 is positioned to translate behind the sled 1220.

After the surgical fastener applying apparatus 1000 (FIG. 1) is manipulated to position the target tissue between the open jaws 1008, 1010 (FIG. 1) of the tool assembly 1004, the jaws 1008, 1010 are approximated using the handle assembly 1002 to clamp the target tissue therebetween and apply a compressive force thereto. Specifically, manipulation of the movable handle $1003_A$ advances the actuation shaft to effectuate corresponding advancement of the control rod. Since the control rod is connected at its distal end to the drive assembly, which includes the aforementioned drive beam 1113, distal movement of the control rod causes corresponding movement of the drive beam 1113, which in turn, forces the anvil 1100 towards the surgical fastener cartridge assembly 1200.

With the tissue securely clamped between the jaws 1008, 1010 (FIG. 1), the surgical fastener applying apparatus 1000 is then fired to eject the surgical fasteners, e.g., the surgical fasteners $100_A$, $100_B$, $100_C$ (FIGS. 9A-11B). To fire the surgical fastener applying apparatus 1000, the movable handle $1003_A$ is again manipulated to cause advancement of the drive assembly, which causes the sled 1220 (FIG. 3) to traverse the cartridge body 1202, and eject the plurality of surgical fasteners 100 from the surgical fastener cartridge assembly 1200. More specifically, as the sled 1220 moves distally, it engages the pushers 1218 (FIGS. 3, 6) to thereby drive the surgical fasteners $100_A$, $100_B$, $100_C$ upwardly, i.e., towards the top wall 1212 of the surgical fastener cartridge body 1202. As the surgical fasteners $100_A$, $100_B$, $100_C$ are driven upwardly, the fastener retention slots 1216 (FIGS. 3, 6) maintain the relative positions thereof.

After passing through the fastener retention slots 1216, the surgical fasteners $100_A$, $100_B$, $100_C$ pass through the tissue and are forced into engagement with the pockets 1104 formed in the tissue contacting surface 1102 of the anvil 1100, thereby achieving, for example, the formed configurations seen in FIGS. 9B, 10B, and 11B, respectively. Upon formation within the tissue, the surgical fasteners $100_A$, $100_B$, $100_C$ limit the blood flow through the tissue immediately adjacent and surrounding the cut-line to thereby effectuate hemostasis, while permitting greater blood flow through the tissue spaced laterally therefrom to minimizing necrosing of the tissue, as discussed above.

While the tool assembly 1004 (FIG. 1) has been discussed in connection with the surgical fastener applying apparatus 1000, which is adapted for use in laparoscopic procedures for performing surgical anastomotic fastening of tissue, the tool assembly 1004 may be adapted for use with any surgical instrument suitable for the intended purpose of applying the plurality of surgical fasteners, e.g., the surgical fasteners 100 (FIG. 2), the surgical fasteners $100_A$ (FIGS. 9A, 9B), the surgical fasteners $100_B$ (FIGS. 10A, 10B), and/or the surgical fasteners $100_C$ (FIGS. 11A, 11B), to a section of tissue, and thereafter, severing the tissue along a cut-line.

For example, the tool assembly 1004 (FIG. 1) may be adapted for use with an end-to-end anastomosis (EEA) apparatus 2000 (FIG. 10), such as that disclosed in commonly assigned U.S. Pat. No. 7,455,676, currently assigned to Tyco Healthcare Group LP, the contents of which are hereby incorporated by reference herein in its entirety. The EEA apparatus 2000 includes a handle assembly 2002 having at least one pivotable actuating handle member 2004, and advancing means 2006. Extending from handle assembly 2002, there is provided a tubular body portion 2008 that terminates in a fastener ejection (tool) assembly 2010 having a circular fastener cartridge 2012 that is configured and dimensioned to retain a plurality of surgical fasteners therein. An anvil shaft 2014 operatively couples an anvil assembly 2016 to the handle assembly 2002 such that the anvil assembly 2016 is repositionable from a location where it is in close cooperative alignment with the fastener cartridge 2012 to a location where it is spaced apart from the fastener staple cartridge 2012.

The tool assembly 2010 includes a fastener ejection member that is positioned within the fastener cartridge 2012. The fastener ejection member includes a distal portion defining concentric rings of peripherally spaced staple pushers that are received within a respective staple retention slot to eject the surgical fasteners from the fastener cartridge 2012. The fastener ejection member is configured and dimensioned to be contacted by a distal end of a driver tube that is operatively connected to the advancing means 2006 through the body portion 2008 such that manipulation of the advancing means effectuates advancement of the driver tube to force the staple pushers into engagement with the plurality of surgical fasteners retained with in the fastener cartridge 2012 to causes ejection thereof.

The tool assembly 1004 (FIG. 1) may also be adapted for use with a surgical stapling apparatus 3000 (FIG. 11), such as that disclosed in commonly assigned U.S. Pat. No. 7,334,717, currently assigned to Tyco Healthcare Group LP, the contents of which are hereby incorporated by reference herein in its entirety. The surgical stapling apparatus 3000 includes a cartridge receiving half-section 3002, which accommodates a plurality of surgical fasteners, and an anvil half-section 3004.

The half-sections 3002, 3004 are pivotally connected via handles 3006, 3008 for approximation during use.

Following approximation of the half-sections 3002, 3004, the surgical fastener applying apparatus 3000 is fired by driving a firing slide 3010 distally through the advancement of a firing lever 3012. Distal movement of the firing slide 3010 causes a plurality of cam bars to engage camming surfaces that interact with a plurality of pushers to expel the plurality of surgical fasteners from the cartridge receiving half-section 3002. The surgical fasteners are positioned on either side of a track which guides a knife during longitudinal movement to thereby sever tissue along a cut-line.

The tool assembly 1004 (FIG. 1) may also be adapted for use with a transverse anastomosis fastening instrument 4000 (FIG. 12), such as that disclosed in commonly owned U.S. Pat. No. 5,964,394, currently assigned to United States Surgical Corporation, the contents of which are hereby incorporated by reference herein in its entirety. The surgical fastener applying apparatus 4000 includes an approximation lever 4001, a movable handle 4002, an elongated portion 4004 that extends distally from the handle 4002, and an arm 4006 that extends from a distal end 4008 of the elongated portion 4004. The surgical fastener applying apparatus 4000 further includes a tool assembly 4010 that includes an anvil 4012 that is orthogonally affixed to the arm 4006, and a surgical fastener cartridge receiver 4014 that is operatively coupled to the distal end 4008 of the elongated portion 4004 for retention of the surgical fastener cartridge 200.

Prior to firing of the surgical fastener applying apparatus 4000, the approximation lever 4001 is actuated to distally advance a drive member that is operatively connected to the surgical fastener cartridge 200 to move the surgical fastener cartridge 200 towards the anvil 4012, which remains stationary, and capture tissue therebetween. Thereafter, the handle 4002 is moved to advance a pusher bar distally through the elongated portion 4004 to cause corresponding movement of a head portion included at the distal end of the pusher bar. The head portion includes a plurality of fingers extending distally therefrom that are configured and dimensioned to engage the cartridge assembly to thereby discharge the plurality of surgical fasteners retained therein. Upon discharge, the surgical fasteners are driven through the tissue and into the anvil 4012 for formation.

It is also envisioned that the tool assembly 1006 (FIG. 1) may also be adapted for use with any of the other surgical fastener applying apparatus discussed in commonly owned U.S. Pat. Nos. 6,045,560; 5,964,394; 5,894,979; 5,878,937; 5,915,616; 5,836,503; 5,865,361; 5,862,972; 5,817,109; 5,797,538; and 5,782,396, the disclosures of which are hereby incorporated by reference herein in their entirety.

In additional embodiments of the present disclosure, the surgical fastener applying apparatus may include a plurality of cam bars for interacting with the pushers to deploy the surgical fasteners. For example, the surgical fastener applying apparatus disclosed in U.S. Pat. No. 5,318,221, the disclosure of which is hereby incorporated by reference herein, in its entirety, has a cam bar adapter that holds a plurality of cam bars and a knife. A channel is advanced through operation of the handle of the apparatus, which drives the cam bars and knife forward. A clamp tube that surrounds the proximal end of the anvil is advanced to clamp the anvil and cartridge together. In another example, the surgical fastener applying apparatus disclosed in U.S. Pat. No. 5,782,396, the disclosure of which is hereby incorporated by reference herein, in its entirety, has an actuation sled. An elongated drive beam is advanced distally through operation of the handle of the apparatus, driving the actuation sled forward. The distal end of the drive beam engages the anvil and the channel that supports the cartridge as the drive beam travels distally, to deploy the staples and clamp the anvil and cartridge together.

Figure 16:
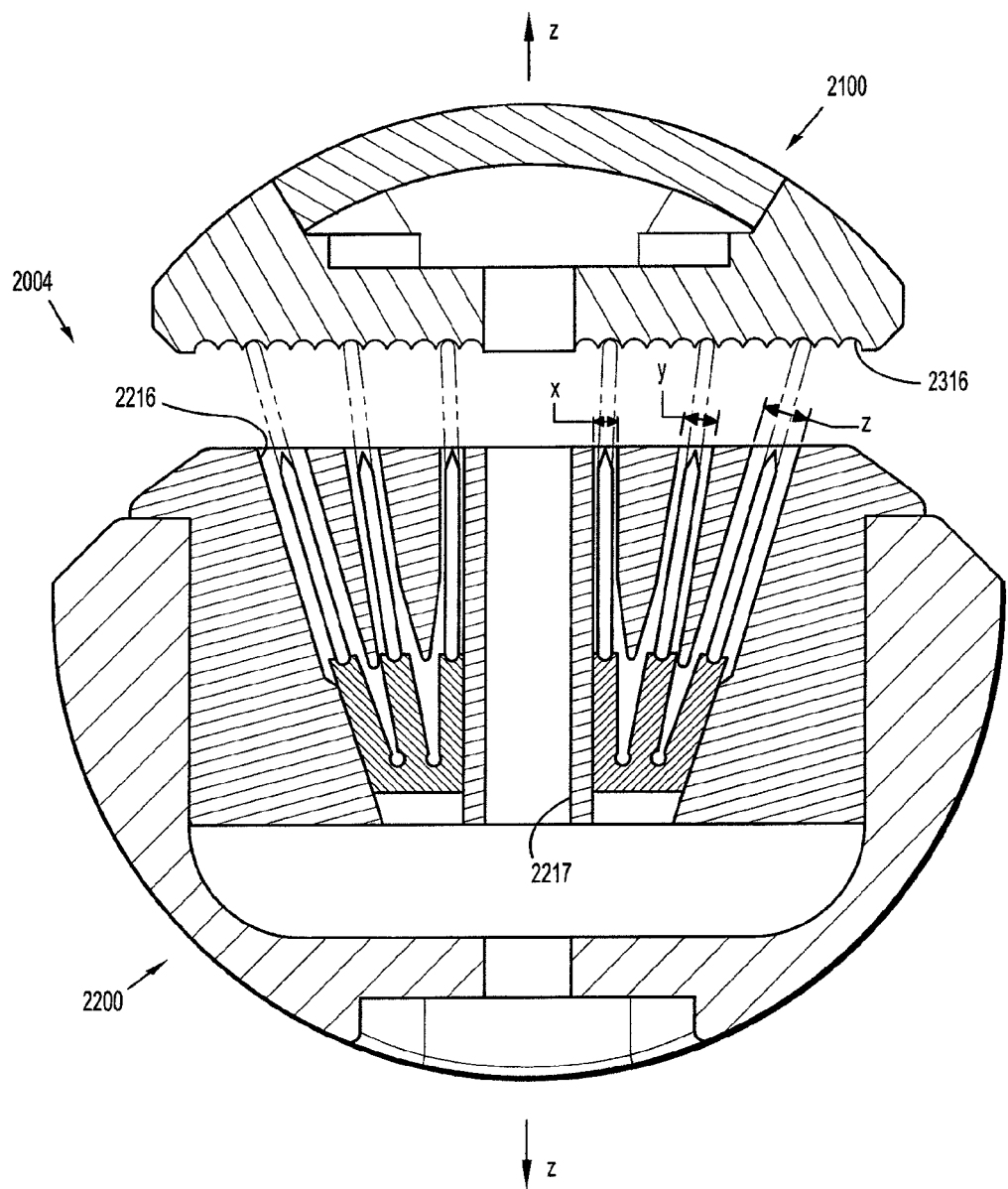
FIG. 16 is a lateral, cross-sectional view of an alternative embodiment of the tool assembly seen in FIG. 1 taken through the fastener pockets formed in the anvil and retention slots formed in the surgical fastener cartridge in accordance with yet another embodiment of the present disclosure.

In a further embodiment of the present disclosure, FIG. 16 shows a cross-sectional view of a tool assembly 2004 having an anvil member 2100 and cartridge assembly 2200. The fastener retention slots 2216 in the outer rows are sized to allow the surgical fasteners 100 to exit the slots 2216 at an angle. The anvil member 2100 has a plurality of forming recesses 2316 for each slot 2216, to ensure formation of the fastener at one or more angled positions with respect to the vertical axis "Z-Z" of the surgical fastener cartridge 2202. The fastener retention slots 2216 in the inner rows, adjacent the longitudinal knife slot 2217 of the surgical fastener cartridge 2202, are sized so that the surgical fasteners 100 exit the retention slots 2216 in a substantially vertical orientation, i.e., along the vertical axis "Z-Z," or at a smaller angle with respect to the vertical axis "Z-Z," as compared to the surgical fasteners 100 in the outer rows of fastener retention slots 2216. The surgical fasteners 100 in each row of fastener retention slots 2216 may be the same size, or alternatively, the surgical fasteners 100 in the in the outer rows of fastener retention slots 2216 may be larger in size when compared to the surgical fasteners 100 in the inner rows of fastener retention slots 2216. For example, the surgical fasteners 100 in the in the outer rows of fastener retention slots 2216 may have longer leg lengths when compared to those of the surgical fasteners 100 in the inner rows of fastener retention slots 2216. The tendency of tissue to extrude in a laterally outward direction with respect to the cartridge body 2202 will encourage the surgical fasteners 100 to angle outwardly, as shown in FIG. 16.

Figure 17:
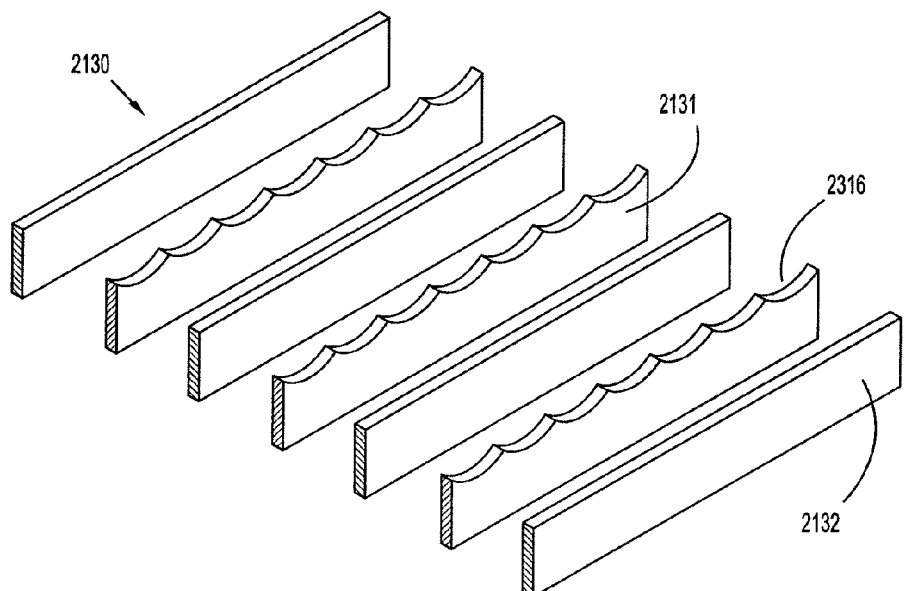
FIG. 17 is perspective view of a plurality of anvil plates, with parts separated, in accordance with still another embodiment of the present disclosure.
Figure 18:
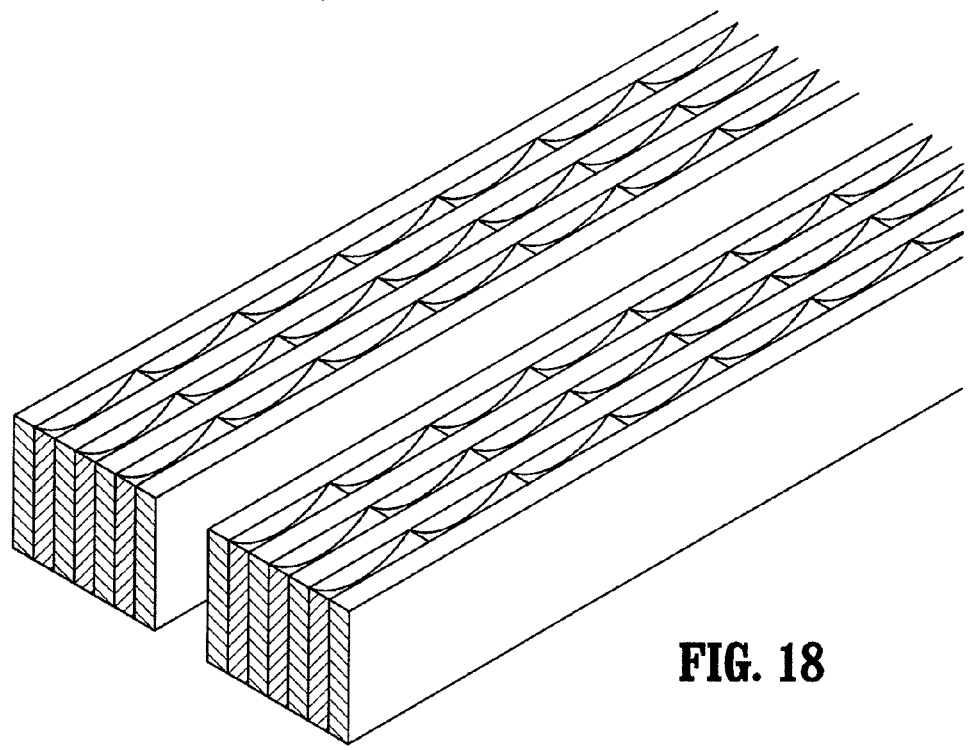
FIG. 18 is a perspective view of the plurality of anvil plates seen in FIG. 17 after assembly.

In certain embodiments, the anvil member 2100 is comprised of a plurality of plates 2130, each having defined therein forming recesses 2316, as shown in FIGS. 17 and 18. The plates 2130 are attached to one another so as to form the anvil member 2100, e.g., via lamination. The forming recesses 2316 may be arranged so that more than one forming recess 2316 corresponds to a fastener retention slot 2216. In this way, a surgical fastener 100 exiting a fastener retention slot 2216 will be directed into, and formed by, one of the forming recess 2316, whether the surgical fastener 100 exits the fastener retention slot 2216 in a substantially vertical, or angled, fashion.

The above description, disclosure, and figures should not be construed as limiting, but merely as exemplary of particular embodiments. It is to be understood, therefore, that the disclosure is not limited to the precise embodiments described, and that various other changes and modifications may be effected by one skilled in the art without departing from the scope or spirit of the disclosure. Additionally, those skilled in the art will appreciate that the elements and features illustrated or described in connection with one embodiment can be combined with those of another, and that such modifications and variations are also intended to be included within the scope of the present disclosure.

What is claimed is:

1. A surgical fastener applying apparatus, comprising:
   an anvil member having a tissue contacting surface;
   a cartridge member extending along a longitudinal axis and being movably coupled to the anvil member, the cartridge member including a plurality of surgical fasteners and a plurality of pushers operatively associated with the plurality of surgical fasteners, each pusher including a base portion and a plurality of pusher plates extending from the base portion such that adjacent pusher plates define an acute angle therebetween; and a sled operably engagable with the plurality of pushers, wherein engagement of the sled with the pushers urges the surgical fasteners toward the anvil member such that a first row of surgical fasteners applies a first compressive force to tissue disposed between the anvil member and the cartridge member, and a second row of surgical fasteners applies a second, different compressive force to tissue disposed between the anvil member and the cartridge member.

2. The surgical fastener applying apparatus of claim 1, wherein the pushers and the surgical fasteners are configured and dimensioned such that the compressive forces are varied along an axis transverse to the longitudinal axis of the cartridge member.

3. The surgical fastener applying apparatus of claim 2, wherein the pushers and the surgical fasteners are configured and dimensioned such that the compressive forces applied to the tissue decrease outwardly relative to a centerline of the cartridge member such that blood flow through tissue nearer to the centerline of the cartridge member is less than blood flow through tissue further from the centerline of the cartridge member.

4. The surgical fastener applying apparatus of claim 2, wherein each pusher plate extends from the base portion to define a different length.

5. The surgical fastener applying apparatus of claim 4, wherein the pusher plates positioned nearer to a centerline of the cartridge member are shorter than the pusher plates positioned further from the centerline.

6. The surgical fastener applying apparatus of claim 5, wherein the plurality of pusher plates includes a first pusher plate, a second pusher plate, and a third pusher plate, the first pusher plate being positioned nearest to the centerline of the cartridge member, the second pusher plate being positioned outwardly of the first pusher plate and further from the centerline, and the third pusher plate being positioned outwardly of the second pusher plate and furthest from the centerline.

7. The surgical fastener applying apparatus of claim 6, wherein the first pusher plate extends from the base portion to define a first length, the second pusher plate extends from the base portion to define a second length, and the third pusher plate extends from the base portion to define a third length, wherein the third length is greater than the second length, and the second length is greater than the first length.

8. The surgical fastener applying apparatus of claim 1, wherein the pusher plates are connected to the base portion at a hinge member configured to allow the pusher plates to diverge as the pushers are driven towards the anvil member by the sled such that the angles described between adjacent pusher plates are increased.

9. The surgical fastener applying apparatus of claim 8, wherein the hinge member is configured as a living hinge.

10. The surgical fastener applying apparatus of claim 1, wherein the cartridge member includes a top wall having a plurality of retention slots formed therein configured and dimensioned to allow the surgical fasteners to pass therethrough during ejection from the cartridge member, each fastener retention slot being aligned with a corresponding pocket formed in the tissue contacting surface of the anvil member.

11. The surgical fastener applying apparatus of claim 10, wherein the surgical fasteners are positioned within the cartridge member to define a distance between penetrating tips thereof and the corresponding pocket formed in the tissue contacting surface of the anvil member.

12. The surgical fastener applying apparatus of claim 11, wherein the surgical fasteners positioned nearer to a centerline of the cartridge member are shorter than the surgical fasteners positioned further from the centerline such that the distance defined between the penetrating tips of the surgical fasteners and the corresponding pockets formed in the tissue contacting surface of the anvil member varies with the distance between the surgical fasteners and the centerline of the cartridge member.

13. The surgical fastener applying apparatus of claim 12, wherein the distance defined between the penetrating tips of the surgical fasteners and the corresponding pockets formed in the tissue contacting surface of the anvil member increases with the distance between the surgical fasteners and the centerline of the cartridge member.

14. The surgical fastener applying apparatus of claim 1, wherein the surgical fasteners are arranged into a plurality of rows including a first row of surgical fasteners positioned nearer to a centerline of the cartridge member, and a second row of surgical fasteners positioned outwardly of the first row and further from the centerline.

15. A surgical fastener applying apparatus, comprising:
an anvil member;
a cartridge member movably coupled to the anvil member and extending along a longitudinal axis, the cartridge member being configured and dimensioned to retain a plurality of surgical fasteners therein; and
at least one pusher positioned within the cartridge member, the at least one pusher being movable to eject the plurality of surgical fasteners from the cartridge member into the anvil member to effectuate formation of the plurality of surgical fasteners such that at least two different compressive forces are applied to tissue, the at least one pusher including a base portion and a plurality of pusher plates connected to the base portion such that the plurality of pusher plates are repositionable relative to a centerline of the cartridge member during movement of the at least one pusher, wherein the pusher plates extend from the base portion such that adjacent pusher plates define an acute angle therebetween.

16. The surgical fastener applying apparatus of claim 1, wherein the plurality of pusher plates are interconnected via the base portion.

17. The surgical fastener applying apparatus of claim 15, wherein the plurality of pusher plates are configured and dimensioned such that the acute angle defined between adjacent pusher plates is varied as the pushers are moved towards the anvil member.

18. The surgical fastener applying apparatus of claim 17, wherein the plurality of pusher plates are configured and dimensioned such that the pusher plates diverge as the pushers are moved towards the anvil member, whereby the acute angle defined between adjacent pusher plates is increased.

19. A pusher configured and dimensioned to eject one or more surgical fasteners from a surgical fastener applying apparatus, the pusher comprising a plurality of pusher plates configured and dimensioned such that at least one of the pusher plates is moved in first and second directions during ejection of the surgical fasteners, the first direction extending along a first axis, and the second direction extending along a second axis transverse in relation to the first axis.

20. The pusher of claim 19, wherein the plurality of pusher plates are interconnected via a common base portion.

21. The pusher of claim 19, wherein the plurality of pusher plates are configured and dimensioned such that adjacent pusher plates define an angle therebetween that is varied during ejection of the one or more surgical fasteners.

22. The surgical fastener applying apparatus of claim 21, wherein the angle defined between adjacent pusher plates is acute.

23. The surgical fastener applying apparatus of claim 21, wherein the plurality of pusher plates are configured and dimensioned such that the pusher plates diverge during ejection of the one or more surgical fasteners, whereby the angle defined between adjacent pushers plates is increased.

\* \* \* \* \*